US006653083B2

(12) United States Patent
Emoto

(10) Patent No.: US 6,653,083 B2
(45) Date of Patent: Nov. 25, 2003

(54) FLUORESCENCE DETECTING DEVICE, METHOD FOR PRODUCING THE SAME, AND FLUORESCENCE DETECTING METHOD EMPLOYING THE SAME

(75) Inventor: Fumiaki Emoto, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/153,377

(22) Filed: May 22, 2002

(65) Prior Publication Data

US 2002/0197634 A1 Dec. 26, 2002

(30) Foreign Application Priority Data

May 22, 2001 (JP) ........................................ 2001-152928
May 22, 2001 (JP) ........................................ 2001-152930

(51) Int. Cl.$^7$ .......................... C12Q 1/68; G01N 33/53; C12M 1/34
(52) U.S. Cl. ................... 435/6; 435/7.1; 435/287.2; 435/288.4; 435/288.7
(58) Field of Search ................ 435/91.1, 91.2, 435/288.7, 6, 7.1, 287.2, 288.4; 436/501; 935/77, 78; 250/458.1, 353, 461.1, 459.1; 356/318, 417, 335–343

(56) References Cited

U.S. PATENT DOCUMENTS 5,973,330 A * 10/1999 Hayashi ................ 250/458.1

FOREIGN PATENT DOCUMENTS

| EP | 0 601 714 | 6/1994 |
| JP | 6-148076 | 5/1994 |
| JP | 7-83900 | 3/1995 |

OTHER PUBLICATIONS

Burns et al in "Microfabricated structures for integrated DNA analysis" PNAS, vol. 93, May 1996 (pp. 5556–5561).*

* cited by examiner

Primary Examiner—Kenneth R. Horlick
(74) Attorney, Agent, or Firm—Merchant & Gould P.C.

(57) ABSTRACT

A fluorescence detecting device is configured so that, on a semiconductor integrated circuit substrate having a photodiode and a signal detecting circuit for detecting charges obtained as a result of photoelectric conversion by the photodiode, a fluorescence reaction vessel where a fluorescence reaction occurs is arranged above the photodiode.

18 Claims, 22 Drawing Sheets

FLUORESCENCE DETECTING DEVICE, METHOD FOR PRODUCING THE SAME, AND FLUORESCENCE DETECTING METHOD EMPLOYING THE SAME

BACKGROUND OF THE INVENTION

1. Field of the Invention

The present invention relates generally to a fluorescence detecting device for detecting a fluorescence reaction, for instance, a fluorescence detecting device suitable for detection, etc., of a specific gene contained in a sample.

2. Related Background Art

Recently, the genome sequence analysis has been developed significantly, and the determination of the whole base sequence of the human genome will be completed in 2003. Besides, the determination of genomes of other creatures is proceeding throughout the world. With this development of the genome analysis, the detection of genes has an increased significance from the viewpoint of the determination of functions of genes, the medical diagnosis, etc. Examples of conventional gene detecting methods include the gene amplification methods represented by the polymerase chain reaction (PCR™) method, while recently the gene detecting method employing DNA chips is used widely.

A DNA chip is an approximately 1 cm×1 cm glass chip, silicon chip, etc. on which a plurality of single-strand DNAs are fixed. Examples of the single-strand DNAs to be fixed include DNAs as etiologic genes. The gene analysis employing a DNA chip is performed, for instance, in the following manner. First of all, a target gene is extracted from cells (for instance, blood cells). Then, the target gene is amplified by the PCR™ method. In the amplification, a fluorescent substance is employed to label an amplification product. A DNA chip is immersed in a solution containing nucleic acid strands labeled with the fluorescent dye, so that hybridization occurs. Thereafter, the DNA chip is washed so that nucleic acids that have not been hybridized are removed.

Subsequently, the DNA chip is irradiated with an excitation light, and the fluorescence is detected. An example of a fluorescence detecting device used herein is shown in FIG. 22. In the device, an excitation light 309 from a light source 305 such as a laser is reflected by a beam splitter 304, and enters an objective lens 306, where the light is focused so as to be incident on a fixed portion 307 of a nucleic acid probe on a DNA chip 308. In the case where a double strand is formed as a result of hybridization, a fluorescent substance is present on the DNA chip 308, and therefore, a fluorescence 310 is emitted upon the irradiation by the excitation light 309. Normally, the fluorescence 310 and the excitation light 309 have a wavelength difference on the order of several tens of nanometers. A part 311 of the fluorescence and a reflected light of the excitation light 309 return to the objective lens, and reach the beam splitter 304. Most of the reflected light of the excitation light 309 is reflected by the beam splitter 304, thereby being directed to the light source side. The part 311 of the fluorescence passes through the beam splitter 304, thereby being directed to a photodetector 301. The part 311 of the fluorescence that has passed through the beam splitter 304 passes through a filter 303 that limits a wavelength, while the reflected light of the excitation light 309 is blocked by the same. Furthermore, the part 311 of the fluorescence passes through a photodetector lens 302 and enters the photodetector 301 for measuring an intensity of the fluorescence, where the fluorescence is detected.

However, the above-described conventional fluorescence detecting device is a large-scale and complex device having a long optical path, through which the fluorescence is lost partly, thereby leading to a problem of low detection sensitivity.

SUMMARY OF THE INVENTION

Therefore, with the foregoing in mind, it is an object of the present invention to provide a fluorescence detecting device that is small in size and has a high sensitivity.

To achieve the foregoing object, a first fluorescence detecting device of the present invention includes a semiconductor integrated circuit substrate and a fluorescence reaction vessel where a fluorescence reaction occurs. The semiconductor integrated circuit substrate includes a photodiode and a signal detecting circuit for detecting charges obtained as a result of photoelectric conversion by the photodiode. The fluorescence reaction vessel is arranged above the photodiode. Here, the fluorescence reaction vessel may be displaced from a position immediately above the photodiode as long as at least a part of the fluorescence generated in the fluorescence reaction vessel enters the photodiode. Normally, at least a part of the fluorescence reaction vessel is positioned above the photodiode.

This device is capable of detecting a fluorescence generated as a fluorescence reaction in the fluorescence reaction vessel by the photodiode arranged under the fluorescence reaction vessel. Therefore, an optical path can be shortened, which results in the improvement of the fluorescence detecting sensitivity and the reduction of the overall size of the device.

The first device preferably is configured as follows. The photodiode and the signal detecting circuit compose one unit cell, and a plurality of the unit cells and a circuit for selecting and driving each of the unit cells are formed on the semiconductor integrated circuit substrate. Besides, a plurality of the fluorescence reaction vessels are provided so as to correspond to the unit cells, respectively. The foregoing configuration allows different tests to be performed in the fluorescence reaction vessels, and allows these tests to be performed with one fluorescence measuring operation.

The first device preferably is configured as follows. The photodiode and the signal detecting circuit compose one unit cell, and a plurality of the unit cells and a circuit for selecting and driving each of the unit cells are formed on the semiconductor integrated circuit substrate. Besides, at least one fluorescence reaction vessel is provided so as to be shared by a plurality of the unit cells. This configuration allows a fluorescence of one fluorescence reaction vessel to be detected by a plurality of photodiodes, and hence, such a photodiode is allowed to have a reduced size. Consequently, each photodiode has a smaller capacitance and internal resistance, thereby causing operations such as reading out charges obtained as a result of photoelectric conversion to be performed at a higher speed, which results in high-speed detection of a fluorescence intensity.

In the foregoing preferable configuration, a plurality of the fluorescence reaction vessels preferably are provided so that each of the fluorescence reaction vessels is shared by a plurality of the unit cells. This configuration allows different tests to be performed in the fluorescence reaction vessels, and allows these tests to be performed with one fluorescence measuring operation.

Furthermore, in the first device, a single-strand DNA may be fixed on a bottom of the fluorescence reaction vessel. In this case, it is used as a DNA chip. Alternatively, an antibody or an antigen may be fixed on a bottom of the fluorescence reaction vessel. Furthermore, in the foregoing fluorescence reaction vessel, a gene amplification reaction such as the PCR™ may be carried out so that an amplification product should be detected by fluorescence.

The first device may be produced by, for instance, preparing a transparent substrate in which a cavity or a hole that serves as the fluorescence reaction vessel is formed, and a semiconductor integrated circuit substrate in which the photodiode and the signal detecting circuit are formed, and adhering the transparent substrate and the semiconductor integrated circuit substrate to each other so that the cavity or the hole is positioned above the photodiode. By this producing method, the fluorescence detecting device can be produced readily. This method is effective particularly in the case where a plurality of fluorescence reaction vessels have to be provided.

A fluorescence detecting method employing the first device is a method in which the excitation light is caused to enter the fluorescence reaction vessel, and a fluorescence generated as a result of the entry of the excitation light is detected by means of the photodiode. In this case, the excitation light preferably is caused to enter the fluorescence reaction vessel from a side thereof, so as to prevent the excitation light from entering the photodiode.

To achieve the aforementioned object, a second fluorescence detecting device of the present invention includes a semiconductor integrated circuit substrate and a fluorescence reaction vessel where a fluorescence reaction occurs. The semiconductor integrated circuit substrate includes a photodiode, a charge transfer section for reading out and transferring charges obtained as a result of photoelectric conversion by the photodiode, a charge accumulating section for accumulating the charges transferred thereto by the charge transfer section, and a signal detecting circuit for detecting charged accumulated in the charge accumulating section. The fluorescence reaction vessel is arranged above the photodiode.

This device is capable of detecting a fluorescence generated as a fluorescence reaction in the fluorescence reaction vessel by the photodiode arranged under the fluorescence reaction vessel. Therefore, an optical path can be shortened, which results in the improvement of the fluorescence detecting sensitivity and the reduction of the overall size of the device. Furthermore, in the present device, among the fluorescence incident on the semiconductor integrated circuit substrate side, light corresponding to an aperture ratio of the photodiode enters the same. The aperture ratio of a photodiode significantly increases with the recent development of the micromachining technology, and this also allows the device of the present invention to be capable of detecting a fluorescence with a high sensitivity.

The second device preferably is configured as follows. One unit cell is composed of the photodiode, the charge transfer section, the charge accumulating section, and the signal detecting circuit, and the semiconductor integrated circuit substrate includes a plurality of the unit cells and a circuit for selecting and driving each of the plurality of the unit cells. Besides, a plurality of the fluorescence reaction vessels are provided so as to correspond to the unit cells, respectively. The foregoing configuration allows different tests to be performed in the fluorescence reaction vessels, and allows these tests to be performed with one fluorescence measuring operation.

The second device preferably is configured as follows. The semiconductor integrated circuit substrate includes a plurality of the photodiodes, the fluorescence reaction vessel is arranged so that a plurality of the photodiodes treats a fluorescence from the fluorescence reaction vessel, and charges obtained as a result of photoelectric conversion by the plurality of the photodiodes are summed by at least one of the charge transfer section and the charge accumulating section. This configuration causes an increased quantity of signal charges to be detected by the signal detecting circuit, thereby enabling the detection with a further improved sensitivity.

In this case, a plurality of the fluorescence reaction vessels may be provided. With the provision of a plurality of fluorescence reaction vessels, if the signal detecting circuit is provided with respect to each fluorescence reaction vessel, variations between the circuits could adversely affect the detection of the signals of the plurality of the fluorescence reaction vessels. Therefore, a singular signal detecting circuit preferably is provided.

Furthermore, in the second device, a single-strand DNA may be fixed on a bottom of the fluorescence reaction vessel. In this case, it is used as a DNA chip. Alternatively, an antibody or an antigen may be fixed on a bottom of the fluorescence reaction vessel. Furthermore, in the foregoing fluorescence reaction vessel, a gene amplification reaction such as the PCR™ may be carried out so that an amplification product should be detected by fluorescence.

The second device can be produced by, for instance, preparing a transparent substrate in which a cavity or a hole that serves as the fluorescence reaction vessel is formed, and a semiconductor integrated circuit substrate in which the photodiode, the charge transfer section, the charge accumulating section, and the signal detecting circuit are formed, and adhering the transparent substrate and the semiconductor integrated circuit substrate to each other so that the cavity or the hole is positioned above the photodiode. By this producing method, the fluorescence detecting device can be produced readily. This method is effective particularly in the case where a plurality of fluorescence reaction vessels have to be provided.

A fluorescence detecting method employing the first device is a method in which the excitation light is caused to enter the fluorescence reaction vessel, and a fluorescence generated as a result of the entry of the excitation light is detected by means of the photodiode. In this case, the excitation light preferably is caused to enter the fluorescence reaction vessel from a side thereof, so as to prevent the excitation light from entering the photodiode.

DETAILED DESCRIPTION OF THE INVENTION

First Embodiment

Figure 1:
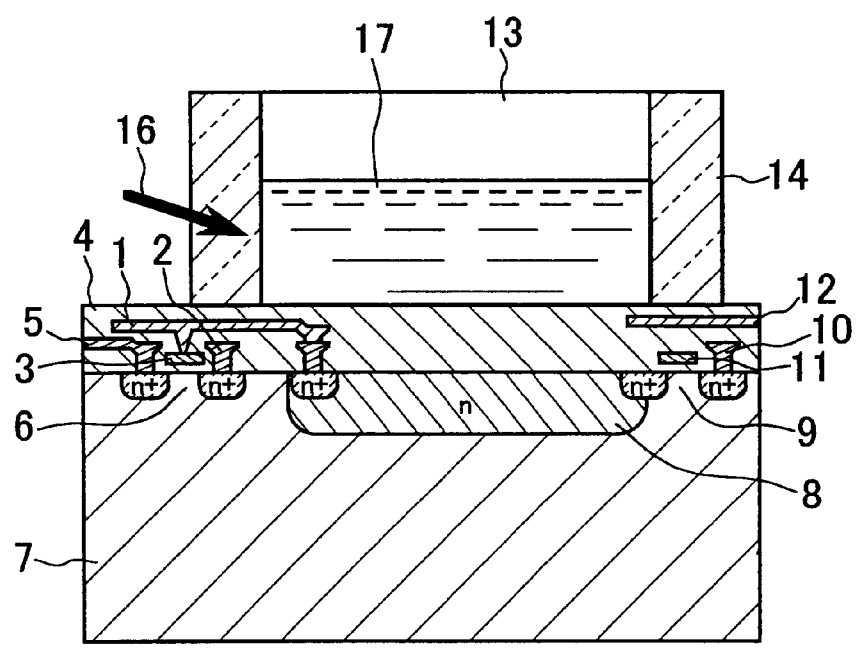
FIG. 1 is a cross-sectional view illustrating an example of a first fluorescence detecting device of the present invention.
Figure 2A:
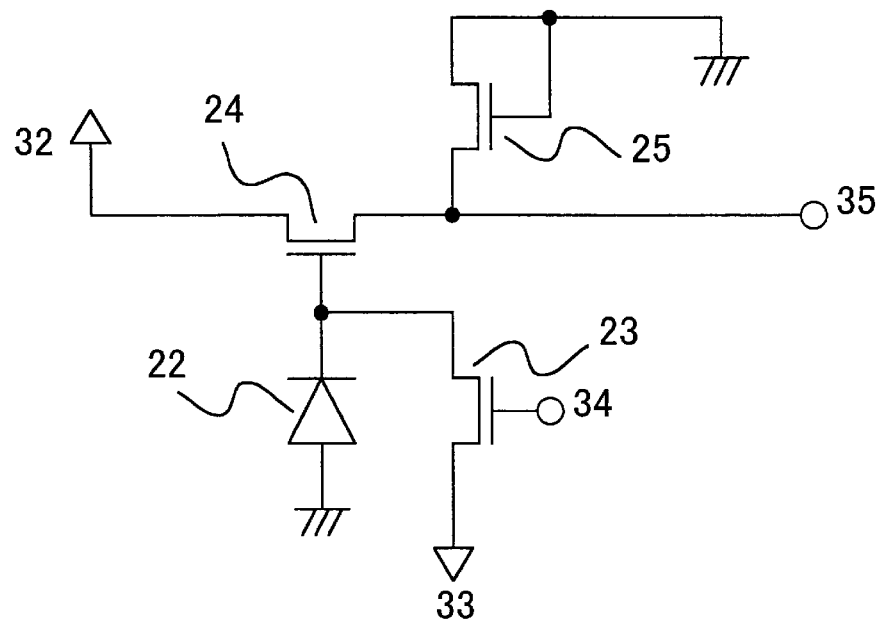
FIG. 2A is a circuit diagram of the device shown in FIG. 1.
Figure 2B:
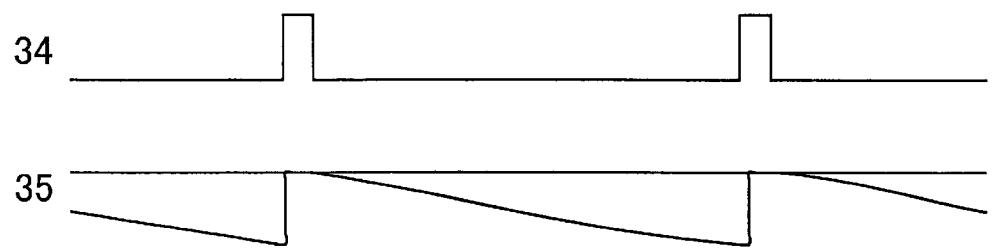
FIG. 2B is a driving timing chart of the same.
Figure 3:
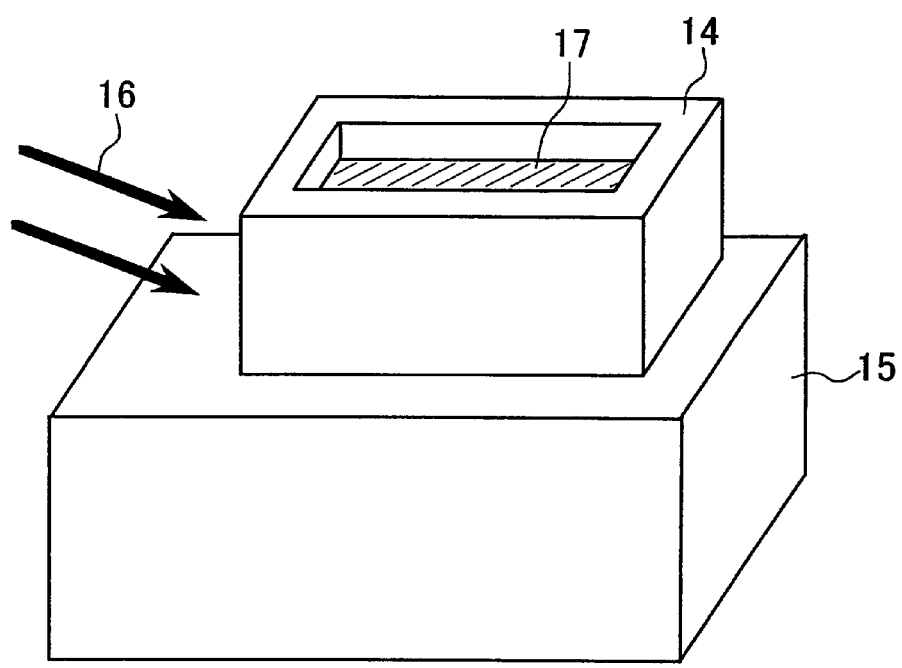
FIG. 3 is a perspective view of the device shown in FIG. 1.

FIGS. 1, 2, and 3 illustrate an example of a basic configuration of a fluorescence detecting device of the present invention. FIG. 1 is a cross-sectional view illustrating a structure of a photodetector part of the foregoing device, and FIG. 3 is a perspective view of the photodetector part of the foregoing device. FIG. 2A is a circuit diagram of a fluorescence detecting circuit of the foregoing device, and FIG. 2B is a driving timing chart of the fluorescence detecting circuit. In FIGS. 1 and 3, the same elements are designated by the same reference numerals.

As shown in FIG. 3, the photodetector part of the foregoing device includes a semiconductor integrated circuit substrate 15 and a fluorescence reaction vessel 13 composed of a transparent container 14, as principal constituent elements. The fluorescence reaction vessel 13 contains a fluorescence reaction solution 17. On the semiconductor integrated circuit substrate 15, a fluorescence detecting circuit is provided. It should be noted that 16 denotes an excitation light entering the fluorescence reaction vessel 13.

As shown in FIG. 2A, the fluorescence detecting circuit includes a photodiode 22, an amplifying transistor 24 whose gate is fed with a voltage of the photodiode 22, a reset transistor 23 that resets charges of the photodiode 22, and a load transistor 25. In the fluorescence detecting circuit, the amplifying transistor 23 and the load transistor 25 constitute a source follower circuit. It should be noted that, in FIG. 2A, 32 denotes a power source of the amplifying transistor 24, 33 denotes a reset power source of the reset transistor 23, and 34 denotes a timing control input terminal of the reset transistor. 35 denotes a signal output terminal of the source follower circuit composed of the amplifying transistor 24 and the load transistor 25.

The fluorescence detecting circuit operates in the following manner. First of all, a cathode of the photodiode 22 is charged by the reset transistor 23 so as to have a positive voltage. Here, the source follower circuit composed of the amplifying transistor 24 and the load transistor 25 has a signal output substantially equal to a gate voltage of the amplifying transistor 24. Since the gate of the amplifying transistor 24 is connected with the cathode of the photodiode 22, the signal output terminal 35 has a voltage substantially equal to a voltage of the reset power source 33 upon resetting. In this state, when light is incident on the photodiode 22, electrons are generated by photoelectric conversion. The electrons are accumulated in a n-type impurity layer 8 forming the photodiode 22, thereby lowering the voltage on the cathode of the photodiode 22. This causes the gate voltage of the amplifying transistor 24 to decrease, thereby causing the voltage of the signal output terminal 35 to decrease also. This sequence of operations can be illustrated by a timing chart as shown in FIG. 2B. More specifically, when a transition to a high level is made at the timing control input terminal 34 of the reset transistor 23 (the transistor is turned on), the signal output terminal 35 is charged so as to have a voltage of the reset power source 33. Thereafter, when a transition to a low level is made at the timing control input terminal 34 of the reset transistor 23 (the transistor is turned off), the photoelectric conversion by the photodiode 22 causes a change in the voltage at the timing control input terminal 34 of the reset transistor 23, and likewise causes a change in the voltage of the signal output terminal 35. The voltage of the signal output terminal 35 indicates an intensity of light subjected to the photoelectric conversion.

FIG. 1 is a cross-sectional view of a photodetector part of the foregoing device. As shown in the drawing, a photodiode, an amplifying transistor, and a reset transistor are formed on this part of the semiconductor integrated circuit substrate 15. The foregoing photodiode is configured so that an n-type impurity layer 8 is formed on a surface part of a p-type silicon substrate 7. This photodiode is connected electrically with the gate 3 of the amplifying transistor 6 via a metal wire 1. 2 and 5 denote a source metal wire and a drain metal wire of the amplifying transistor 6, respectively. The foregoing photodiode is connected electrically with the reset transistor 9. 11 denotes a gate of the reset transistor 9, and 10 denotes a reset power source line. 12 denotes a metal layer that shields elements other than the photodiode (for instance, active elements such as the reset transistor). 4 denotes an interlayer insulation layer. The fluorescence reaction vessel 13 is arranged on the foregoing photodiode.

In the foregoing device, when excitation light 16 is applied to the fluorescence reaction vessel 13, a part of a fluorescence generated in the fluorescence reaction vessel 13 is incident on the photodiode, where the light is subjected to the photoelectric conversion, whereby signal charges are generated. The signal charges are accumulated in the n-type impurity layer 8, and a voltage according to the foregoing charges is fed to the gate of the amplifying transistor 6. Here, it should be noted that any charges remaining in the photodiode are discharged by the reset transistor before the signal charges are accumulated. Thereafter the photodetector circuit operates as described above, whereby light subjected to the photoelectric conversion is detected.

In the foregoing device, the semiconductor integrated circuit substrate 15 is produced by, for instance, the MOS (metal-oxide film-semiconductor) process for producing an integrated circuit (IC) with a silicon substrate 7, but it is not limited to this in the present invention. The semiconductor integrated circuit substrate 15 may be, for instance, a polycrystalline silicon integrated circuit substrate, an amorphous silicon integrated circuit substrate, or a GaAs integrated circuit substrate formed on a glass substrate. Furthermore, the transparent container 14 composing the fluorescence reaction vessel 13 can be made of, for instance, quartz, polymethyl methacrylate (PMMA), etc., but the material is not limited to these. Any material may be used as long as it has a high light transmittance and emits the least possible fluorescence. Furthermore, in the foregoing device, the interlayer insulation film 4, that is, the surface part of the semiconductor integrated circuit substrate 15, preferably is flattened by the chemical machining process (CMP) or the like. In the case where the semiconductor integrated circuit substrate 15 has a flat surface, it is possible to allow the excitation light to enter the fluorescence reaction vessel in a direction parallel with the foregoing surface, thereby preventing the excitation light from directly entering the n-type impurity layer 8 composing the photodiode. As a result, the intensity of background light can be suppressed.

The operation of detecting the fluorescence of a gene by means of the foregoing device is performed, for instance, in the following manner. First of all, a single-strand DNA with the complementary sequence to that of a gene as a target of the detection is fixed in the fluorescence reaction vessel. The fixing method is not limited particularly, and any usual method may be used. A DNA (oligonucleotide) may be synthesized directly on a bottom of the fluorescence reaction vessel, or alternatively, the bottom of the fluorescence reaction vessel may be coated with a material to which a DNA tends to be bound, and a cloned DNA or a PCR™ product may be fixed thereon. Then, a sample solution is introduced into the fluorescence reaction vessel. Here, in the case where the target DNA itself is labeled with a fluorescent dye such as Cy3, the fluorescence reaction vessel may be washed after the sample solution is introduced. Even in the case where the target DNA is not labeled with a fluorescent dye, a fluorescent intercalator such as SYBR®-Green or the like may be put in the sample solution or the fluorescence reaction vessel. Then, the excitation light is projected into the fluorescence reaction vessel, for example, from a side thereof. In the case where the single-strand DNA fixed on the bottom of the fluorescence reaction vessel and the target DNA are hybridized thereby forming a double strand, a fluorescence is emitted radially by either the fluorescent intercalator or the fluorescent label of the target DNA, which has entered in the double strand. In the case where the SYBR®-Green is used, a second harmonic generation (SHG) laser with a wavelength of 473 nm may be projected thereto as the excitation light. A part of the fluorescence emitted is detected by the photodiode, and converted by the photoelectric conversion into electric signals. Thereafter, the aforementioned operations are carried out by the semiconductor integrated circuit substrate, whereby electric signals according to the foregoing fluorescence are output.

In the case where the foregoing device is configured so as to include a plurality of photodiodes and single-strand DNAs of a plurality of types are fixed accordingly, a plurality of samples can be analyzed in one detecting operation.

Furthermore, though a single-strand DNA is fixed on the bottom of the fluorescence reaction vessel in the foregoing case described as an example, an antibody or an antigen may be fixed instead. In this case, a sample solution of a fluorescent-labeled antibody or antigen is put in the fluorescence vessel. Thereafter, the sample solution is removed, and the excitation light for fluorescence is projected thereto. Here, in the case where an antigen-antibody complex is formed, a fluorescence is emitted, which is detected by a photodiode. Alternatively, the enzyme immunoassay (ELISA®) may be applied. In this case, a first antibody is fixed on the bottom of the fluorescence reaction vessel, to which a sample solution containing an antigen is supplied. Then, an antigen-antibody complex is formed. Further, a second antibody, which is enzyme-labeled, is supplied thereto, so that a complex is formed in a sandwich structure in which the first antibody, the antigen, the second antibody are arranged in the stated order. Then, a substrate that is changed to a fluorescent substance by an enzyme reaction is added thereto, so as to be subjected to an enzyme reaction. The excitation light is projected thereto, and a fluorescence of the fluorescent substance produced is detected by the photodiode. It should be noted that in the fluorescence detection by the antibody-antigen reaction, in the case where a plurality of photodiodes are provided, a plurality of antibodies or antigens may be fixed so that they can be analyzed at once.

Furthermore, in this device, the gene amplification such as the PCR™ may be performed. In this case, a sample solution containing a target DNA, and a buffer solution containing a pair of primers that can be hybridized with both ends of the target DNA, a heat-resistant DNA polymerase (Taq®DNA polymerase, etc.), dNTPs, a fluorescent intercalator, and the like are put in the foregoing fluorescence reaction vessel. Then, by repeating a series of steps of the denaturation of the target DNA with heat, the annealing of the primers, and the elongation of the DNA polymerase, the target DNA is amplified. Since the fluorescent intercalator is bound to an amplification product obtained, irradiation with the excitation light causes a fluorescence to be emitted, which can be detected by the photodiode.

Second Embodiment

Figure 4:
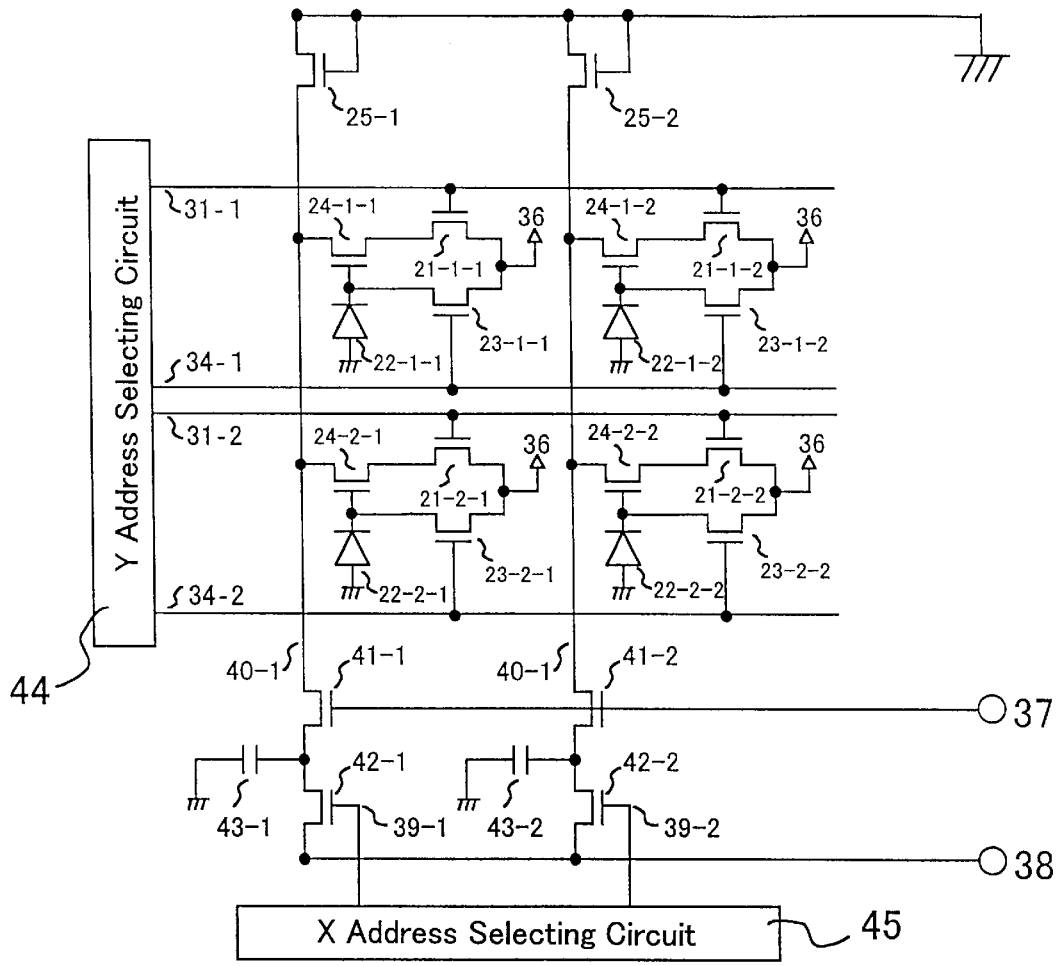
FIG. 4 is a circuit diagram illustrating another example of the device of the present invention.
Figure 5:
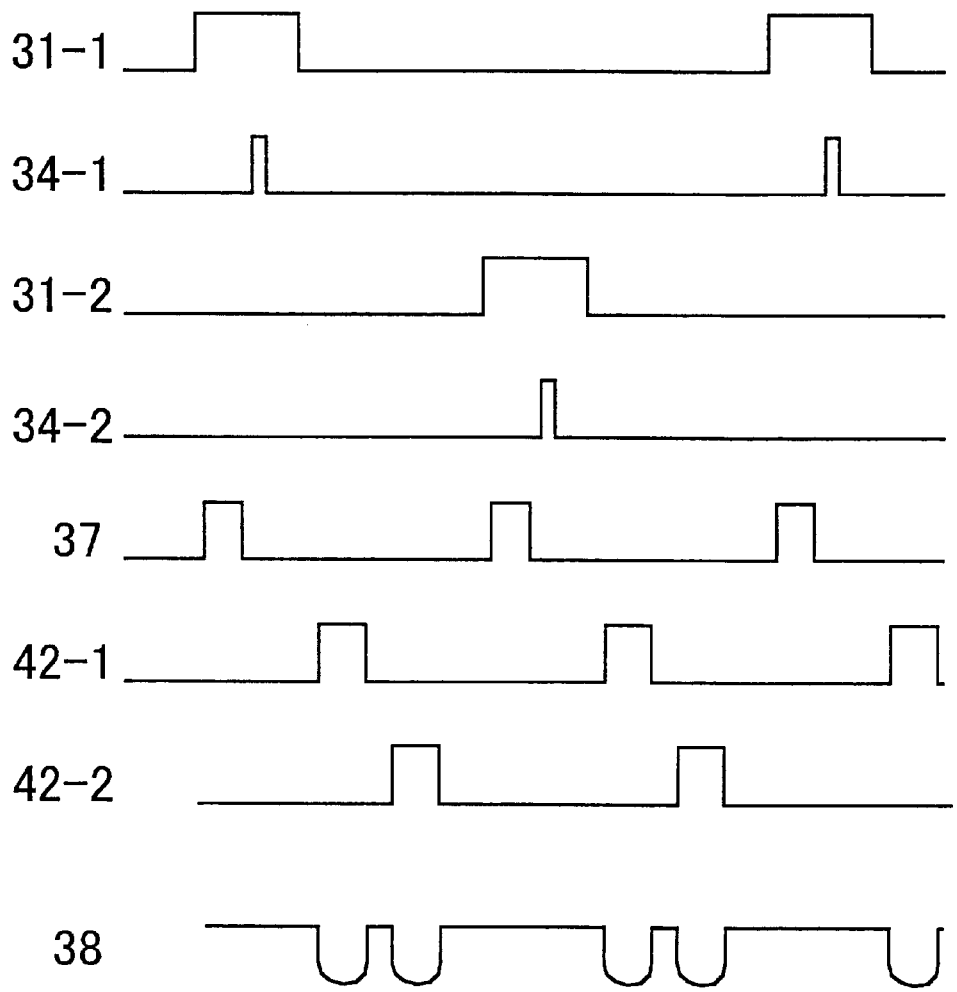
FIG. 5 is a driving timing chart of the device shown in FIG. 4.
Figure 6:
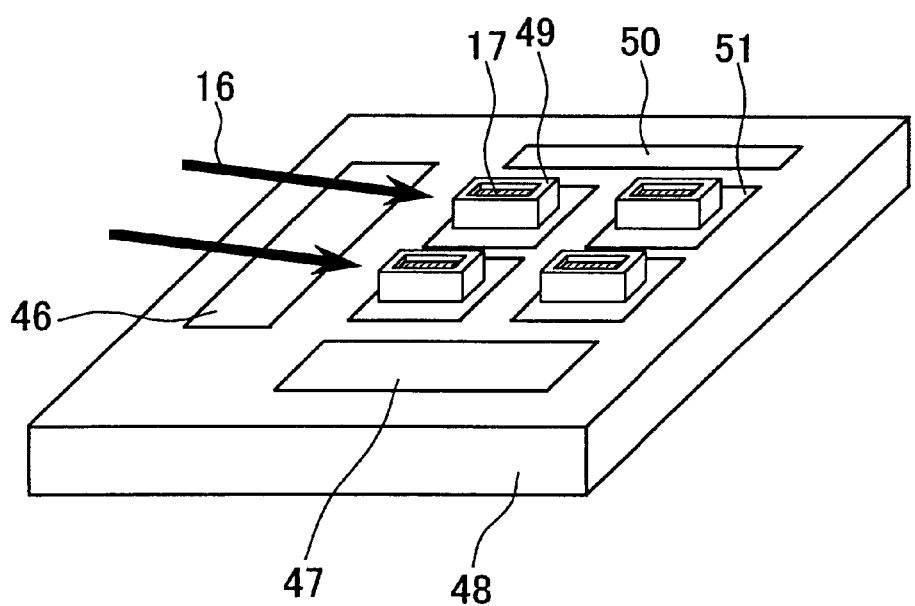
FIG. 6 is a perspective view of the device shown in FIG. 4.

An example of a device including a plurality of unit cells, each of which has a fluorescence reaction vessel, is described with reference to FIGS. 4, 5 and 6. FIG. 4 is a circuit diagram of the device, FIG. 5 is a driving timing chart of the device, and FIG. 6 is a perspective view of the device. In FIGS. 4, 5 and 6, the same elements are designated by the same reference numerals.

As shown in FIG. 6, the foregoing device includes a semiconductor integrated circuit substrate 48 and a plurality of fluorescence reaction vessels 49 containing a fluorescence reaction solution 17, as principal constituent elements. On the semiconductor integrated circuit substrate 48, a plurality of unit cells 51 are provided, and each fluorescence reaction vessel 49 is arranged on a photodiode in each unit cell. In the drawing, 46 denotes a Y address selecting circuit. 47 denotes an X address driving circuit, which is composed of an X address selecting circuit, a signal fetching transistor, an amplification signal accumulating capacitor, and the like. 48 denotes the semiconductor integrated circuit substrate. 49 denotes the fluorescence reaction vessel. 17 denotes the fluorescence reaction solution. 50 denotes a load transistor, and 51 denotes the unit cell of the fluorescence detecting device. As shown in the drawing, an excitation light 16 is directed in parallel with a surface of the semiconductor integrated circuit substrate 48, and enters the fluorescence reaction vessels 49 from sides thereof.

As shown in FIG. 4, the unit cells include photodiodes 22-1-1 to 22-2-2, amplifying transistors 24-1-1 to 24-2-2 for amplifying signals obtained as a result of the photoelectric conversion by the photodiodes, reset transistors 23-11 to 23-2-2 for resetting signals accumulated in the foregoing photodiodes, and Y address selecting transistors 21-1-1 to 21-2-2 for selecting a Y address line from which a signal is read. One unit cell is composed of, for instance, the photodiode 22-1-1, the amplifying transistor 24-1-1, the reset transistor 23-1-1, and the Y address selecting transistor 21-1-1. It should be noted that though the unit cells are arranged in a two-dimensional 2×2 array in the foregoing circuit diagram, the configuration is not limited to this. More unit cells may be provided, or the unit cells may be arranged linearly.

As shown in the drawing, the Y address lines 31-1 and 31-2 drawn from the address selecting circuit are connected with gates of the Y address selecting transistors 21-1-1 to 21-2-2. Reset control lines 34-1 and 34-2 are connected with gates of the reset transistors 23-1-1 to 23-2-2, and sources of the amplifying transistors 24-1-1 to 24-2-2 are connected to X address signal lines 40-1 and 40-2. Ends on one side of the X address signal lines 40-1 and 40-2 are connected to the load transistors 25-1 and 25-2, respectively. Ends on the other side of the same are connected via the signal fetching transistors 41-1 and 41-2 for fetching signals from the unit cells to the amplification signal accumulating capacitors 43-1 and 43-2 for accumulating signals, as well as via the X address selecting transistors 42-1 and 42-2, which are selected according to X address selection pulses 39-1 and 39-2 supplied from the X address selecting circuit 45, to a signal output line 38. The signal fetching transistors 41-1 and 41-2 commonly are subjected to gate control by a fetching timing pulse line 37.

The following will describe an operation of this device, while referring to a timing chart of FIG. 5. When a transition to a HI level is made at the Y address line 31-1, the Y address selecting transistors 21-1-1 and 21-1-2 are turned on, thereby causing the amplifying transistor 24-1-1 and the load transistor 25-1 to constitute a source follower circuit, and causing the amplifying transistor 24-1-2 and the load transistor 25-2 to constitute a source follower circuit. As a result, voltages substantially equal to cathode voltages of the photodiodes 22-1-1 and 22-1-2, that is, gate voltages of the amplifying transistors 24-1-1 and 24-1-2, appear at the X address signal lines 40-1 and 402, respectively. Here, a transition to a HI level is made at the fetching timing pulse terminal 37 so as to turn on the signal fetching transistors 41-1 and 41-2, and signal charges, which are products obtained by multiplying the voltages appearing at the X address signal lines 40-1 and 40-2 with a capacitance of the amplification signal accumulating capacitor 43-1 and 43-2, are accumulated in the amplification signal accumulating capacitor 43-1 and 43-2, respectively. After signals are accumulated in the amplifying signal accumulating capacitors 43-1 and 43-2, a transition to a LO level is made at the fetching timing pulse line 37, so as to turn off the signal fetching transistors 41-1 and 41-2. Thereafter, a transition to a HI level is made at the reset control line 34-1, so as to turn on the reset transistors 23-1-1 and 23-1-2, whereby signal charges accumulated in the photodiodes 22-1-1 and 22-1-2 are resetted. Subsequently, with the X address selection pulses 39-1 and 39-2, the X address selecting transistors 42-1 and 42-2 are turned on successively, so that signal charges accumulated in the amplification signal accumulating capacitors 43-1 and 43-2 are read out successively from the signal output terminal 38. The operation described above is performed also with respect to the unit cells of the next Y address line. Thus, signals are detected from the unit cells arrayed two-dimensionally.

It should be noted that, though the unit cells and the fluorescence reaction vessels are arranged in a two-dimensional 2×2 array in the drawing, the arrangement is not limited to this. More unit cells and fluorescence reaction vessels than those in number may be provided, or they may be arranged linearly.

It should be noted that the other configurations, conditions, operations and the like of the foregoing device are identical to those in the first embodiment described above.

Third Embodiment

Figure 7:
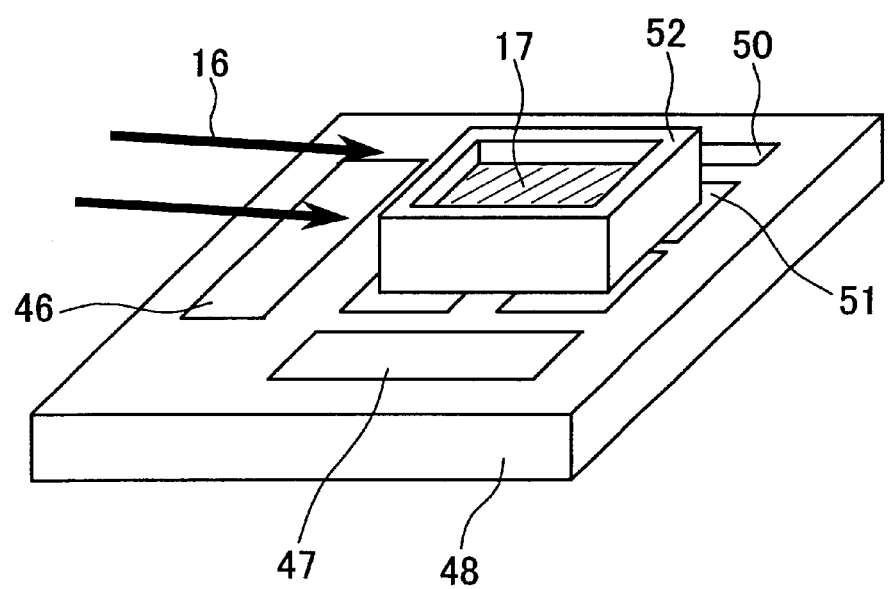
FIG. 7 is a perspective view illustrating still another example of a first fluorescence detecting device of the present invention.

FIG. 7 is a perspective view illustrating still another example of the fluorescence detecting device of the present invention. It should be noted that in FIG. 7, the same elements as those in FIG. 6 are designated by the same reference numerals. This device includes a plurality of unit cells, and is configured so that one fluorescence reaction vessel corresponds to a plurality of unit cells.

As shown in FIG. 7, this device includes a semiconductor integrated circuit substrate 48 and a fluorescence reaction vessel 52 containing a fluorescence reaction solution 17, as principal constituent elements. A plurality of unit cells 51 are provided on the semiconductor integrated circuit substrate 48, and one fluorescence reaction vessel 52 is provided over a plurality of unit cells. In other words, the foregoing device is configured so that a plurality of photodiodes correspond to the fluorescence reaction vessel 52. In this device, a fluorescence in the fluorescence reaction vessel can be determined by, for instance, summing charges accumulated by the plurality of photodiodes during or after a detecting operation.

With this configuration of the device in which a plurality of photodiodes correspond to one fluorescence reaction vessel, each photodiode is allowed to have a reduced size, thereby to have a smaller capacitance. This makes it possible to execute an operation for reading out charges from photodiodes at a high speed.

Though the foregoing drawing illustrates a device having one fluorescence reaction vessel, the configuration is not limited to this, and the device may include a plurality of fluorescence reaction vessels. In this case, the fluorescence reaction vessels may be arranged so that each corresponds to a plurality of unit cells.

It should be noted that the other configurations, conditions, operations, and the like of the this device are identical to those in the first or second embodiment described above.

Fourth Embodiment

Figure 8:
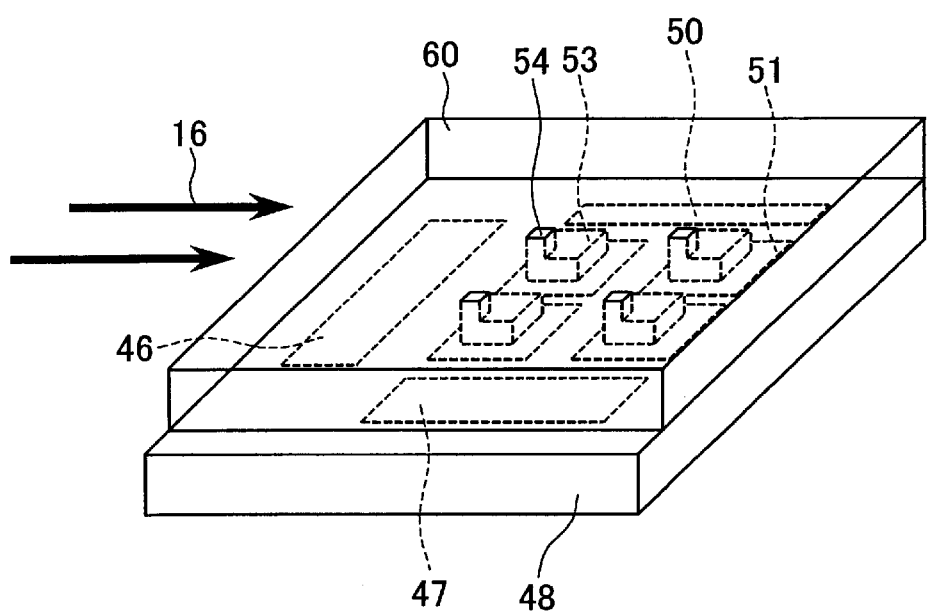
FIG. 8 is a perspective view illustrating still another example of a first fluorescence detecting device of the present invention.
Figure 9:
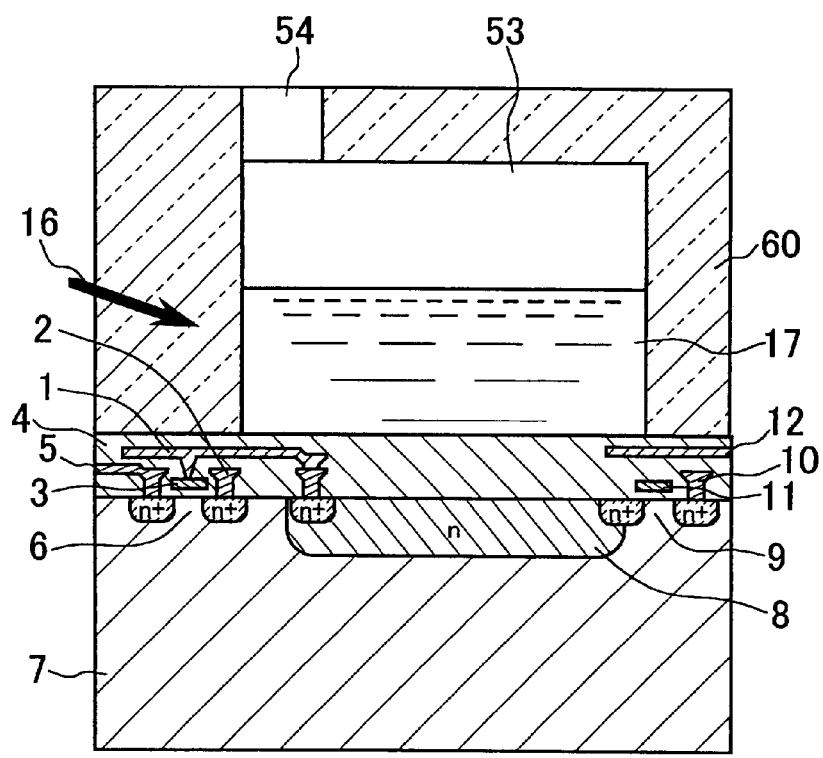
FIG. 9 is a cross-sectional view of a unit cell portion of the device shown in FIG. 8.

FIGS. 8 and 9 illustrate an example of a fluorescence detecting device that is produced by adhering with each other a transparent substrate in which cavities or holes are provided to serve as fluorescence reaction vessels and a semiconductor integrated circuit substrate. FIG. 8 is a perspective view illustrating a configuration of the device, and FIG. 9 is a cross-sectional view of a unit cell portion of the foregoing device. In FIG. 8, the same elements as those in FIG. 6 are designated by the same reference numerals. Further, in FIG. 9, the same elements as those in FIG. 1 are designated by the same reference numerals.

As shown in the drawings, the foregoing device is produced by adhering a transparent substrate 60 having four cavities to a semiconductor integrated circuit substrate 48. They are adhered to each other so that the cavities are positioned above photodiodes of unit cells 51. Each cavity is composed of a fluorescence reaction vessel 53 and an inlet 54 through which a sample and the like is introduced. Thus, tops of the fluorescence reaction vessels 53 are closed with only their inlets 54 opened. This reduces transpiration, splashing, etc. of the fluorescence reaction solution.

It should be noted that the other configurations, operations, driving operations, and the like of the foregoing device are identical to those of the device according to the first, second, or third embodiment described above.

Fifth Embodiment

Figure 10:
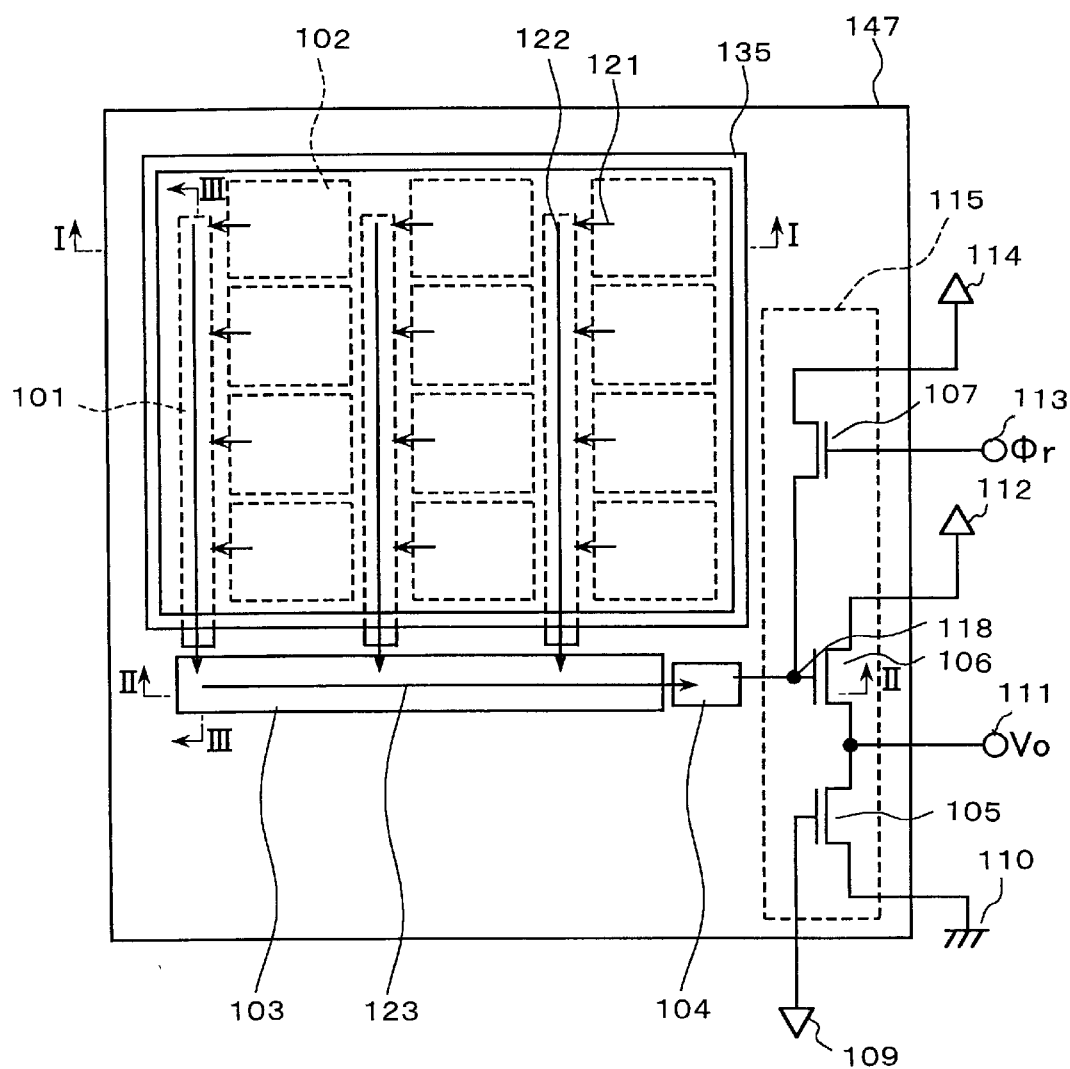
FIG. 10 is a plan view illustrating an example of a second fluorescence detecting device of the present invention.
Figure 11:
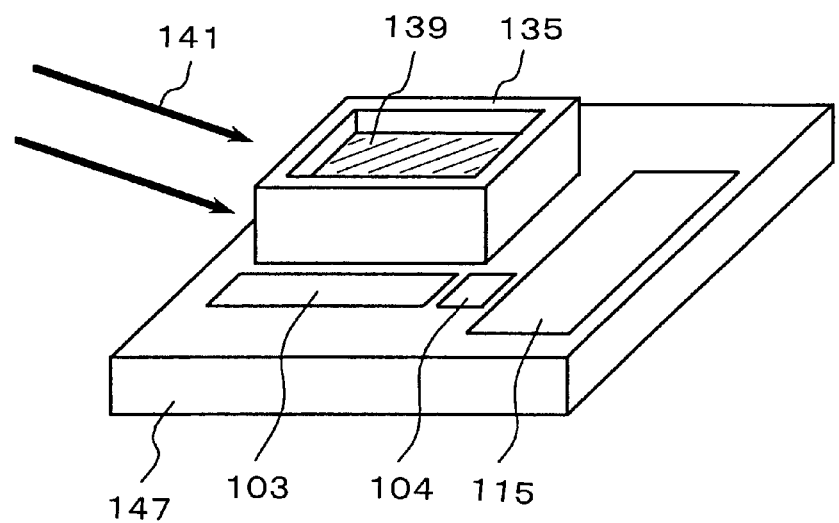
FIG. 11 is a perspective view of the device shown in FIG. 10.
Figure 12:
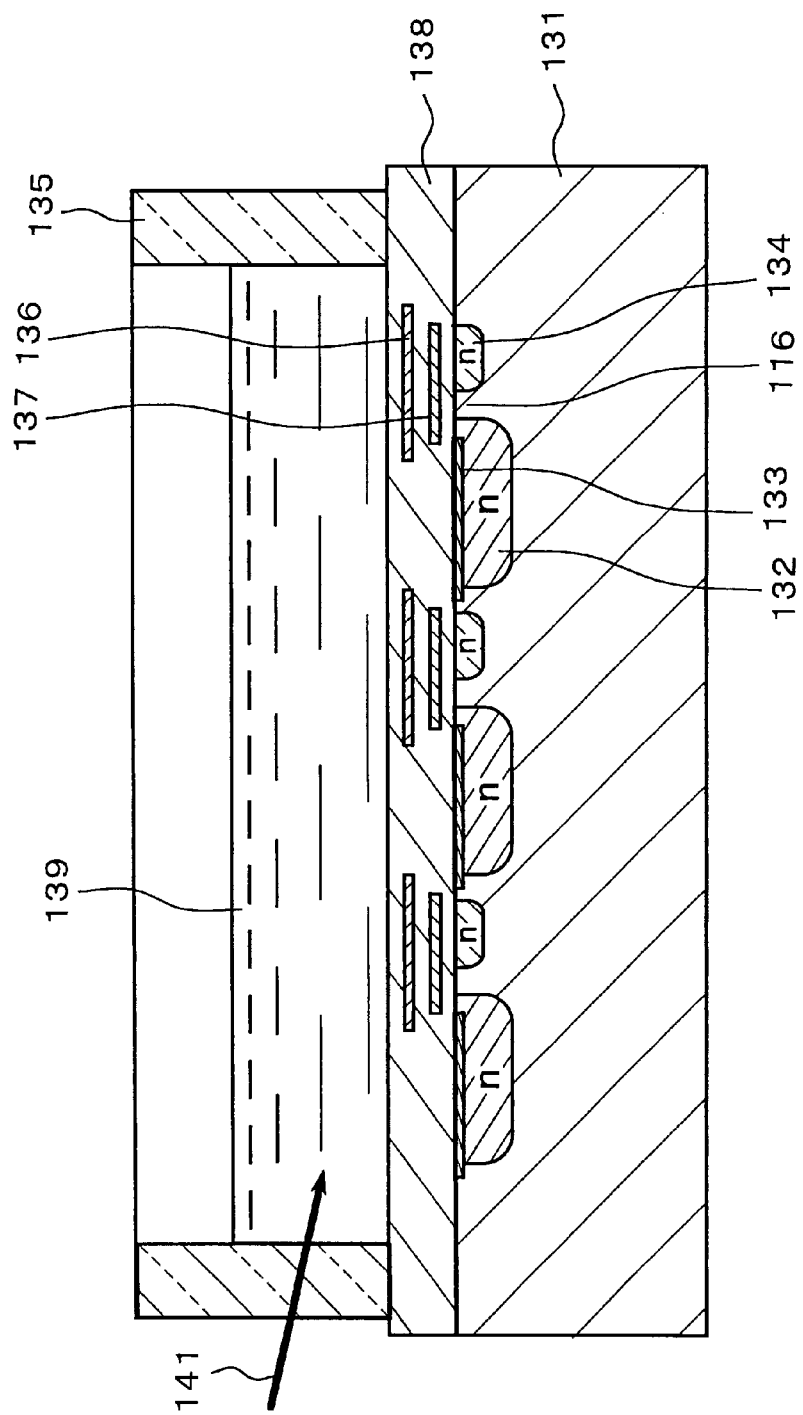
FIG. 12 is a cross-sectional view taken along a line I—I in FIG. 10.
Figure 13:
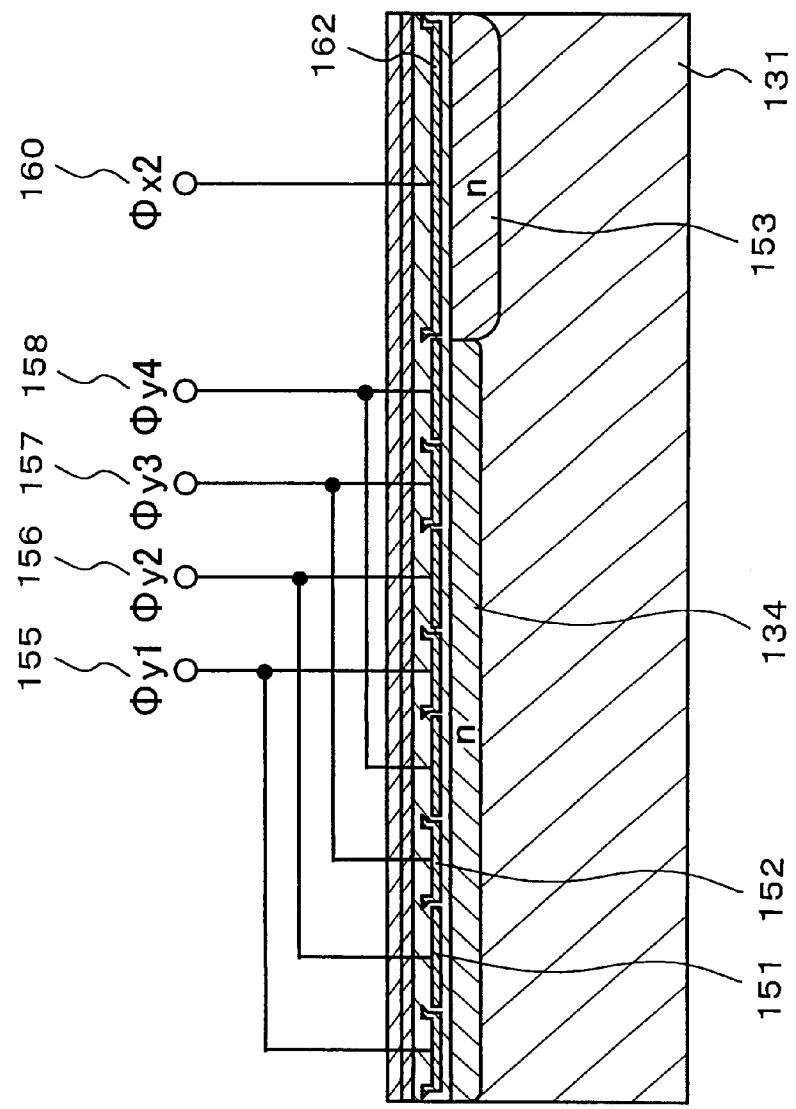
FIG. 13 is a cross-sectional view taken along a line II—II in FIG. 10.
Figure 14:
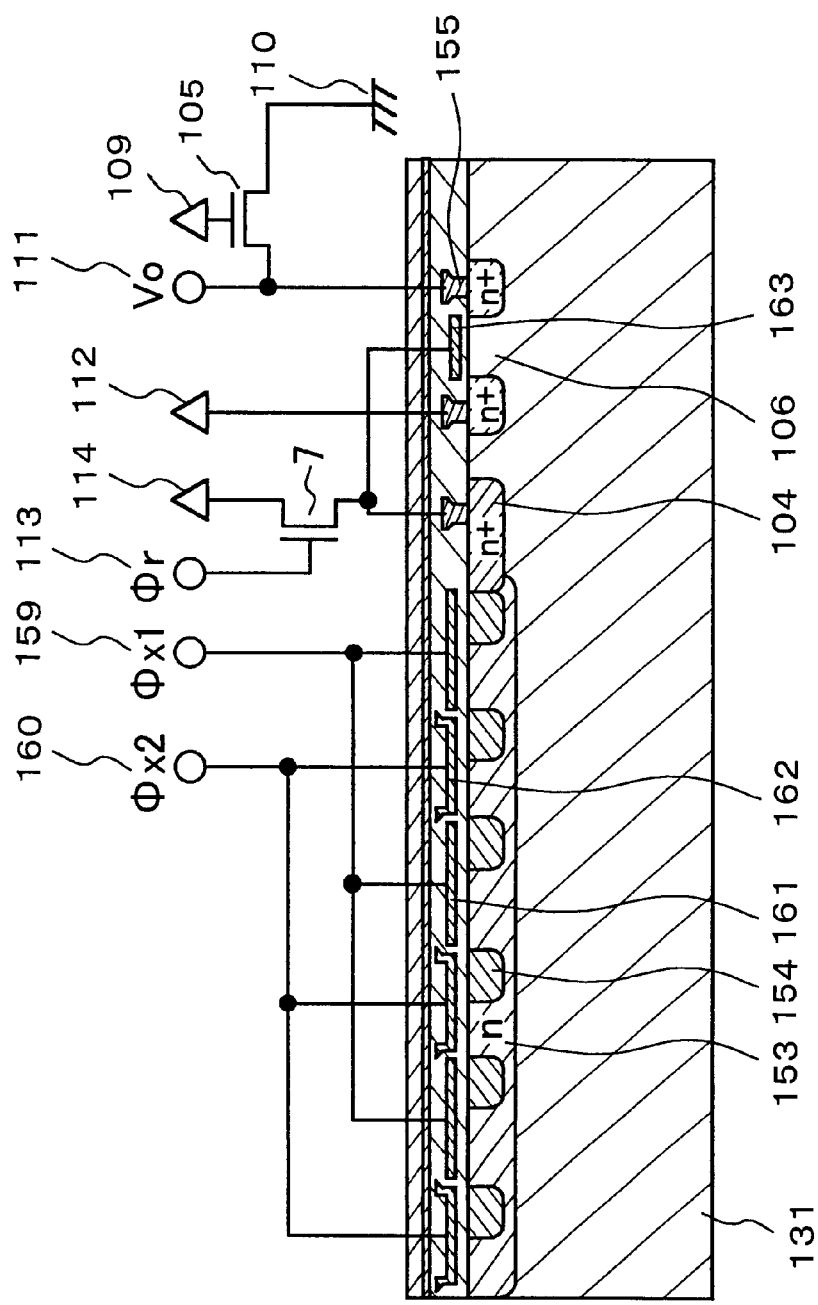
FIG. 14 is a cross-sectional view taken along a line III—III in FIG. 10.
Figure 15:
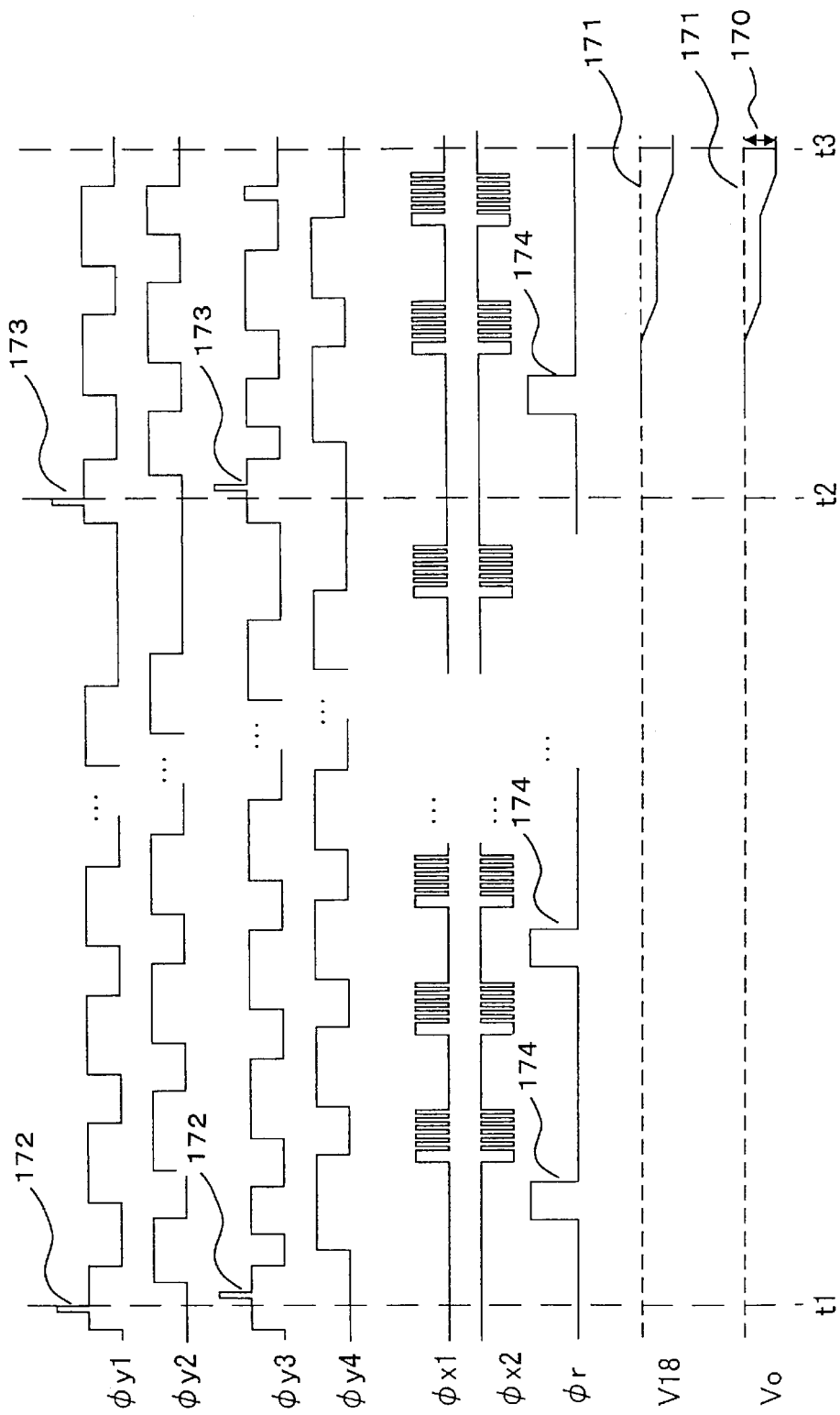
FIG. 15 is a circuit driving timing chart of the device shown in FIG. 10.

FIGS. 10 to 15 illustrate still another example of the fluorescence detecting device of the present invention. FIG. 10 is a plan view illustrating a configuration of the device, and FIG. 11 is a perspective view of the device. FIG. 12 is a cross-sectional view taken along a line I—I in FIG. 10, FIG. 13 is a cross-sectional view taken along a line II—II in FIG. 10, and FIG. 14 is a cross-sectional view taken along a line III—III in FIG. 10. Further, FIG. 15 is a circuit driving timing chart of the foregoing device. In these drawings, the same elements are designated by the same reference numerals.

As shown in FIGS. 10 and 11, a photodetector part of the foregoing device includes a semiconductor integrated circuit substrate 147 and a fluorescence reaction vessel 135 made of a transparent material, as principal constituent elements. The foregoing fluorescence reaction vessel 135 contains a fluorescence reaction solution 139. On the foregoing semiconductor integrated circuit substrate 147, there are formed a plurality of photodiodes 102 arrayed two-dimensionally, a Y transfer section 101, an X transfer section 103, a charge accumulating section 104, and an amplifying circuit 115. The Y transfer section 101 and the X transfer section 103 are so-called charge coupled devices (CCD), each of which has a plurality of transfer electrodes arrayed in a transfer direction. The amplifying circuit 115 is a signal detecting circuit for detecting charges accumulated in the charge accumulating section 104, and includes an amplifying transistor 106 whose gate is fed with a voltage of the charge accumulating section 104, a reset transistor 107 that resets charges of the charge accumulating section 104, and a load transistor 105. In the amplifying circuit 115, the amplifying transistor 106 and the load transistor 105 constitute a source follower circuit. It should be noted that in FIG. 10, 118 denotes a gate of the amplifying transistor 106, 114 denotes a reset power source, 113 denotes a reset pulse ($\phi$r) terminal, 109 denotes a gate power source of the load transistor, 112 denotes a power source of the source follower circuit, 110 denotes a ground power source, and 111 denotes a signal output terminal.

When an excitation light 141 is applied to the fluorescence reaction vessel 135, a fluorescence is generated, and when the fluorescence enters the photodiodes 102, it is subjected to the photoelectric conversion, whereby charges are accumulated therein. The charges thus obtained by the photoelectric conversion and accumulated are moved to the Y transfer section 101 by a readout operation 121. The charges moved to the Y transfer section 101 are transferred to the X transfer section 103 by a transfer operation 122 of applying a pulse voltage to a plurality of transfer electrodes of the Y transfer section 101. Then, the charges transferred to the X transfer section 103 are transferred to the charge accumulating section 104 by a transfer operation 123 of applying a pulse voltage to a plurality of transfer electrodes of the X transfer section 103. Through these operations, the charges obtained by the photoelectric conversion by the photodiodes 102 are accumulated in the charge accumulating section 104.

The following will describe an operation performed by the amplifying circuit 115. Before charges are accumulated in the charge accumulating section 104, a pulse that turns on the reset transistor 107 is fed from the reset pulse terminal 113 to a gate of the reset transistor 107, so that the charge accumulating section 104 is charged to have a voltage of the reset power source 114. This reset operation causes the charge accumulating section 104 to have a voltage of the reset power source 114. Thereafter, the charges generated by the photoelectric conversion of the fluorescence are accumulated in the charge accumulating section 104, thereby causing a change in the voltage of the charge accumulating section 104. The charge accumulating section 104 is connected with the gate 118 of the amplifying transistor 106, and hence, the gate 118 has a voltage equal to that of the charge accumulating section 104. Since the amplifying transistor 106 and the load transistor 105 compose a source follower circuit, the signal output terminal 111 (Vo) has a voltage that is substantially equal to the voltage of the gate 118. With this voltage of the signal output terminal 111 (Vo), an intensity of the fluorescence can be determined. In other words, when the fluorescence is intense, charges obtained by the photoelectric conversion increase, thereby lowering the voltage of the charge accumulating section 104. Consequently, the voltage of the signal output terminal 111 (Vo) drops. When the fluorescence is weak, charges obtained by the photoelectric conversion decrease, thereby causing the voltage of the signal output terminal 111 (Vo) to approximate a voltage of the reset power source 114, which is a high voltage.

FIG. 12 is a cross-sectional view taken along the line I—I in FIG. 10. As shown in the drawing, this part includes a p-type semiconductor substrate 131, photodiodes, each of which is composed of an n-type impurity layer 132 and a p+ impurity layer 133, readout transistors 116 for reading out charges generated by the photoelectric conversion, n-type impurity layers 134 that serve as channels of the Y transfer section 101, an interlayer insulation film 138, polysilicon layers 136, shielding metal layers 137, and a fluorescence reaction vessel 135. The polysilicon layers 136 serve as transfer electrodes of the Y transfer section 101, as well as gates of the readout transistor 116. The fluorescence from the fluorescence reaction solution 139 is subjected to the photoelectric conversion at the photodiode, and signal charges generated therein are accumulated in the n-type impurity layer 132 of each photodiode. It should be noted that before accumulating the signal charges, the n-type impurity layers 132 are depleted. The p+ impurity layers 133 are made in a non-depleted state, so as to perform a function in absorbing an excitation light 141 that has a wavelength shorter than that of the fluorescence. This eliminates the influence of the excitation light. Then, a high voltage is applied to the polysilicon layers 136 so as to move the charges accumulated in the n-type impurity layers 132 to the n-type impurity layers 134 of the Y transfer section 101.

FIG. 13 is a cross-sectional view taken along the line II—II in FIG. 10. This part includes the p-type semiconductor substrate 131, the n-type impurity layer 134 that serves as a channel of the Y transfer section 101, an n-type impurity layer 153 that serves as a channel of the X transfer section 103, a first transfer electrode 151 of the Y transfer section 101, a second transfer electrode 152 of the Y transfer section 101, and a second transfer electrode 162 of the X transfer section 101. The first transfer electrode 151 of the Y transfer section 101 is connected with a $\phi$y2 terminal 156 and a $\phi$y4 terminal 158, and the second transfer electrode 152 of the Y transfer section 101 is connected with a $\phi$y1 terminal 155 and a $\phi$y3 terminal 157. This allows the Y transfer section 101 to be actuated according to a four-phase pulse. Before charges are transferred, the n-type impurity layer 134 serving as a channel of the Y transfer section 101 and the n-type impurity layer 153 serving as a channel of the X transfer section 103 are depleted.

FIG. 14 is a cross-sectional view taken along the line III—III in FIG. 10. This pair includes the p-type semiconductor substrate 131, the n-type impurity layer 153 and n-type impurity layers 154 that serve as channels of the X transfer section 103, a first transfer electrode 161 of the X transfer section 103, a second transfer electrode 162 of the X transfer section 103, the charge accumulating section 104 composed of a high-density n-type impurity layer, and the amplifying transistor 106. The impurity density of the n-type impurity layer 153 is set lower than that of the n-type impurity layers 154. Before charges are transferred, the n-type impurity layers 153 and 154 serving as channels of the X transfer section 103 are depleted. The first transfer electrode 161 of the X transfer section 103 is connected with a φx1 terminal 60, and the second transfer electrode 162 of the X transfer section 103 is connected with a φx2 terminal 159. This allows the X transfer section 103 to be actuated according to a two-phase pulse. Charges transferred from the Y transfer section 101 are accumulated in the n-type impurity layer 154 under the second transfer electrode 162 of the X transfer section 103, then, successively transferred rightward as view in the drawing, thereby being moved to the charge accumulating section 104 finally. Thus, charges in the photodiode are accumulated in the charge accumulating section 104.

As shown in FIG. 10, the charge accumulating section 104 is connected with the gate 118 of the amplifying transistor 106 and with the reset transistor 107. The amplifying transistor 106, in combination with the load transistor 105, constitutes a source follower circuit, and is connected with the power source 112 and the signal output terminal 111. The reset transistor 107 has a source connected with the reset power source 114, and discharges charges in the charge accumulating section 104 when the reset pulse (φr) 113 is supplied to a gate thereof, so as to cause the charge accumulating section 104 to have the voltage of the reset power source 114.

The following will describe operations of the foregoing device, while referring to the driving timing chart of FIG. 15. φy1, φy2, φy3, and φy4 are pulses supplied to a plurality of transfer electrodes of the Y transfer section 101, which operate to transfer charges obtained by the photoelectric conversion at the photodiodes to the Y transfer section 101, and to transfer charges having been transferred to the Y transfer section 101 to the X transfer section 103. The transfer electrodes supplied with the φy1 and φy3 also serve as gates of transistors that transfer charges from the photodiodes to the Y transfer section 101. When high-level voltages 172 and 173 are applied to the transfer electrodes, charges are read out of the photodiodes to the Y transfer section 101. Further, a voltage at a middle level and a voltage at a low level are applied repeatedly, and charges are transferred from the Y transfer section 101 to the X transfer section 103. φx1 and φx2 are pulses supplied to a plurality of transfer electrodes of the X transfer section 103. When middle-level and low-level voltages are applied repeatedly to the plurality of transfer electrodes of the X transfer section 103, the charges having been transferred to the X transfer section 103 are transferred to the charge accumulating section 104. φr is a pulse applied to a gate of the reset transistor 7. As shown in the drawing, the reset transistor 107 makes a transition to the ON state when a high-level voltage 174 is applied, and a voltage of the charge accumulating section 104 is charged in the reset power source 114. Thus, charges are discharged. The high-level voltage 174 preferably is applied immediately before charges obtained by the photoelectric conversion of a fluorescence are transferred to the charge accumulating layer 104, since this allows unnecessary charges to be removed. V18 denotes a voltage of the gate 118 of the amplifying transistor 106, which drops when charges are transferred to the charge accumulating layer 104.

Vo denotes a voltage of the signal output terminal 111, which behaves substantially in the same manner as that of the voltage of the gate 118 of the amplifying transistor 106, which is an input to the source follower circuit. The intensity of a fluorescence can be measured according to a degree of a voltage drop 170 at a time t3. Here, high-level voltages 171 as V18 and Vo are indicative of a voltage of the reset power source 114. Furthermore, a period from a time t1 until a time t2 is a period during which charges obtained by the photoelectric conversion of a fluorescence are accumulated in the photodiodes.

In the device according to the present embodiment also, as in the first embodiment, the semiconductor integrated circuit substrate can be made of, for instance, a silicon substrate, but it is not limited to this in the present invention. The semiconductor integrated circuit substrate may be, for instance, a polycrystalline silicon integrated circuit substrate, an amorphous silicon integrated circuit substrate, or a GaAs integrated circuit substrate formed on a glass substrate. In this device also, the semiconductor integrated circuit substrate preferably has a flattened surface. Besides, the fluorescence reaction vessel can be formed by arranging a transparent container on a semiconductor integrated circuit substrate, as shown in the drawing. The transparent container may be made of, for instance, quartz, or polymethyl methacrylate (PMMA), but the material is not limited to these. Any material may be used as long as it has a high light transmittance and emits the least possible fluorescence.

Furthermore, as in the fourth embodiment, the device of the present embodiment may be produced by adhering to each other a transparent substrate in which cavities or holes are provided to serve as fluorescence reaction vessels and a semiconductor integrated circuit substrate.

It should be noted that the fluorescence detecting operation employing the foregoing device is performed as in the same manner as the operation explained in the description of the first embodiment.

Sixth Embodiment

Figure 16:
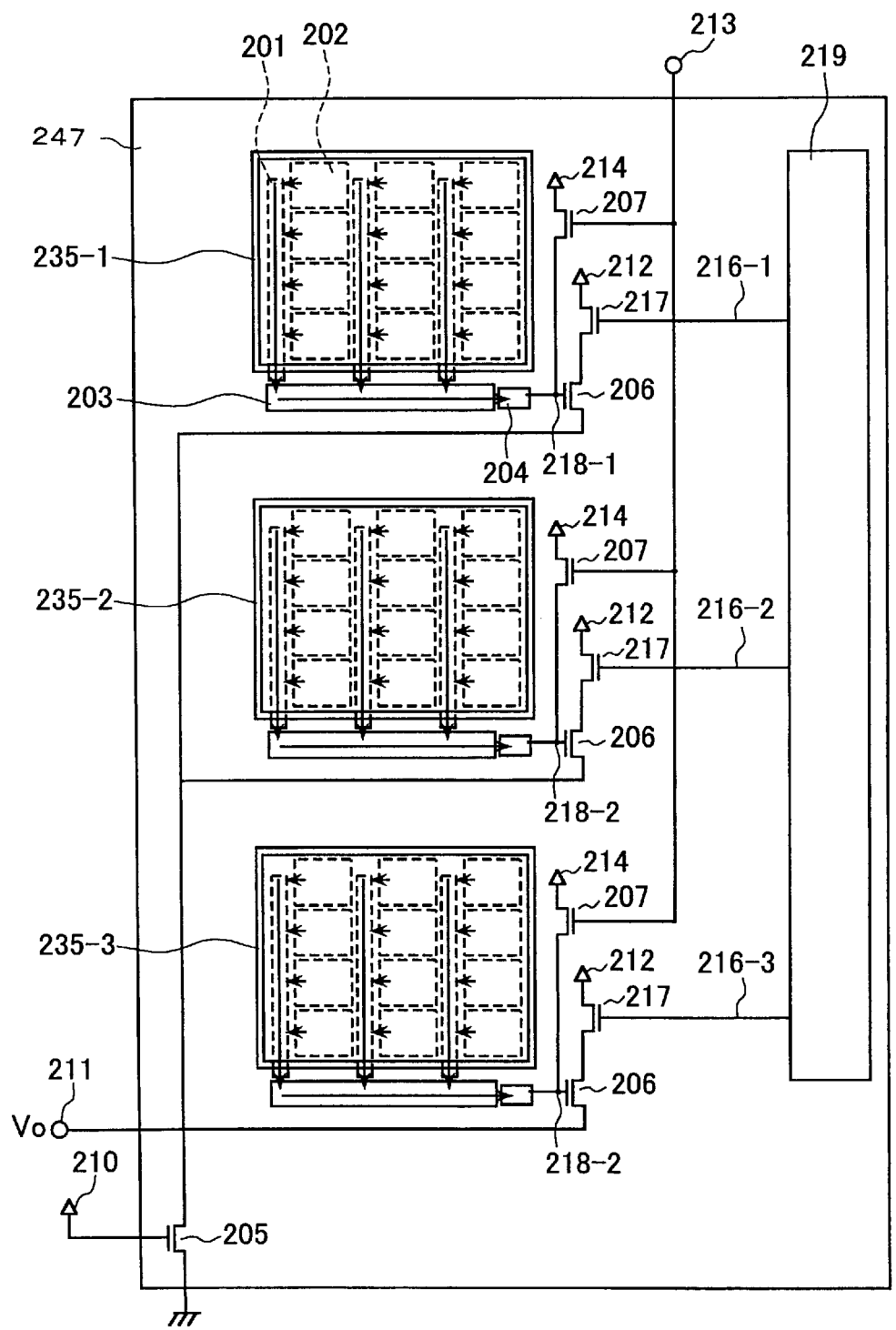
FIG. 16 is a plan view illustrating still another example of a second fluorescence detecting device of the present invention.
Figure 17:
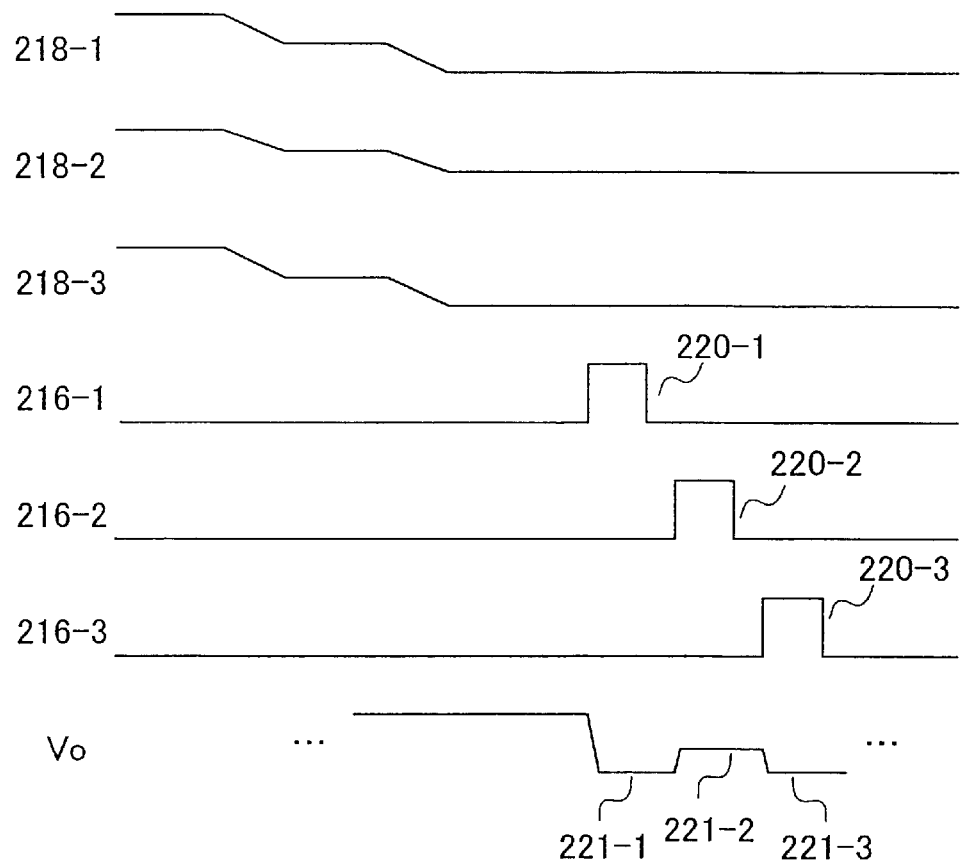
FIG. 17 is a circuit driving timing chart of the device shown in FIG. 16.

FIG. 16 is a plan view illustrating still another example of the fluorescence detecting device of the present invention. This device includes a plurality of unit cells, each of which has fluorescence reaction vessels. FIG. 17 is a driving timing chart of the foregoing device. In these drawings, the same members as those shown in FIGS. 10 to 15 are designated by the same reference numerals.

As shown in FIG. 16, the foregoing device includes a semiconductor integrated circuit substrate 247 and a plurality of fluorescence reaction vessels 235-1, 235-2, and 235-3 containing a fluorescence reaction solution, as its principal constituent elements. On the semiconductor integrated circuit substrate 248, a plurality of unit cells are provided, and one fluorescence reaction vessel is arranged on photodiodes of each unit cell. The drawing illustrates an example in which three unit cells are arranged linearly, but the arrangement is not limited to this. More unit cells may be provided, and the unit cells may be arranged linearly.

Each unit cell includes a plurality of photodiodes 202 arranged in a two-dimensional matrix, a Y transfer section 201, an X transfer section 203, a charge accumulating section 4, a reset transistor 207, an amplifying transistor 206, and a selecting transistor 217. Furthermore, in each unit cell, a source of the reset transistor 207 is connected to a reset power source 214, and a source of the selecting transistor 217 is connected to a power source 212. It should be noted that in the foregoing drawing, 218-1, 218-2, and 218-3 denote control gates of the amplifying transistor 206 of each unit cell. It should be noted that this drawing illustrates an example in which photodiodes are arranged two-dimensionally in a 4×3 matrix in each unit cell, but the arrangement is not limited to this. More photodiodes may be provided, and the photodiodes may be arranged two-dimensionally.

As shown in the drawing, selecting lines 216-1, 216-2, and 216-3 drawn from the selecting circuit 219 are connected to a gate of the selecting transistor 217. A reset control line 213 is connected with gates of the reset transistors 207. In the same drawing, 205 denotes a load transistor that, in combination with the amplifying transistor 206, constitutes a source follower, and is configured so as to adjust a resistance according to a voltage of a power source 210 applied to the control gate.

The same driving operation as that in the device according to the third embodiment is executed with respect to each unit cell of the foregoing device, so as to transfer charges to the charge accumulating layer 204, and this causes voltages of the control gates 218-1, 218-2, and 218-3 of the amplifying transistors 206 of each unit cells to drop, as shown in FIG. 17. Thereafter, when selection pulses 220-1, 220-2, and 220-3 for selecting a unit cell are fed to the selecting lines 216-1, 216-2, and 216-3 connected with control gates of the selecting transistors 217, respectively, signals 221-1, 221-2, and 221-3 of the respective unit cells appear at the signal output terminal 221.

It should be noted that the other configurations, operations, conditions, driving operations, and the like of the foregoing device are identical to those of the aforementioned device according to the fifth embodiment.

Seventh Embodiment

Figure 18:
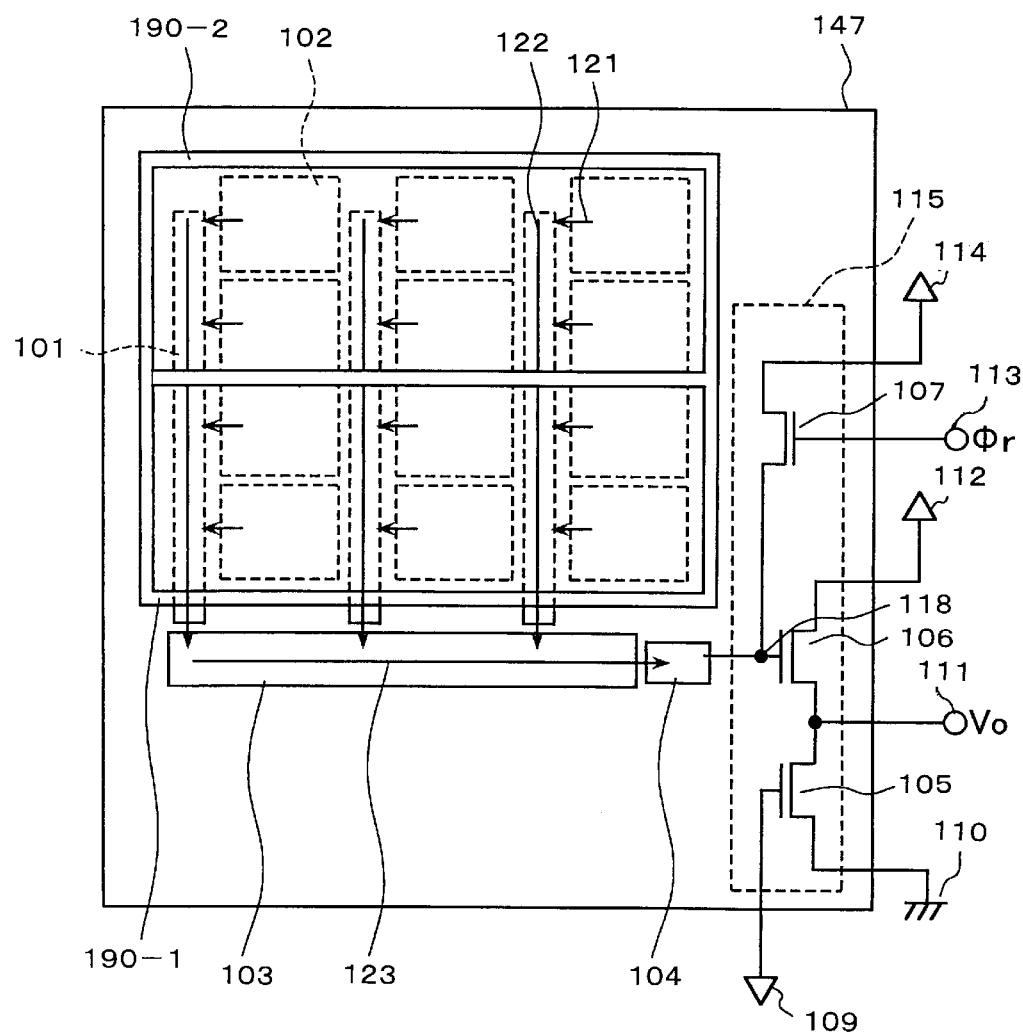
FIG. 18 is a plan view illustrating still another example of a second fluorescence detecting device of the present invention.
Figure 19:
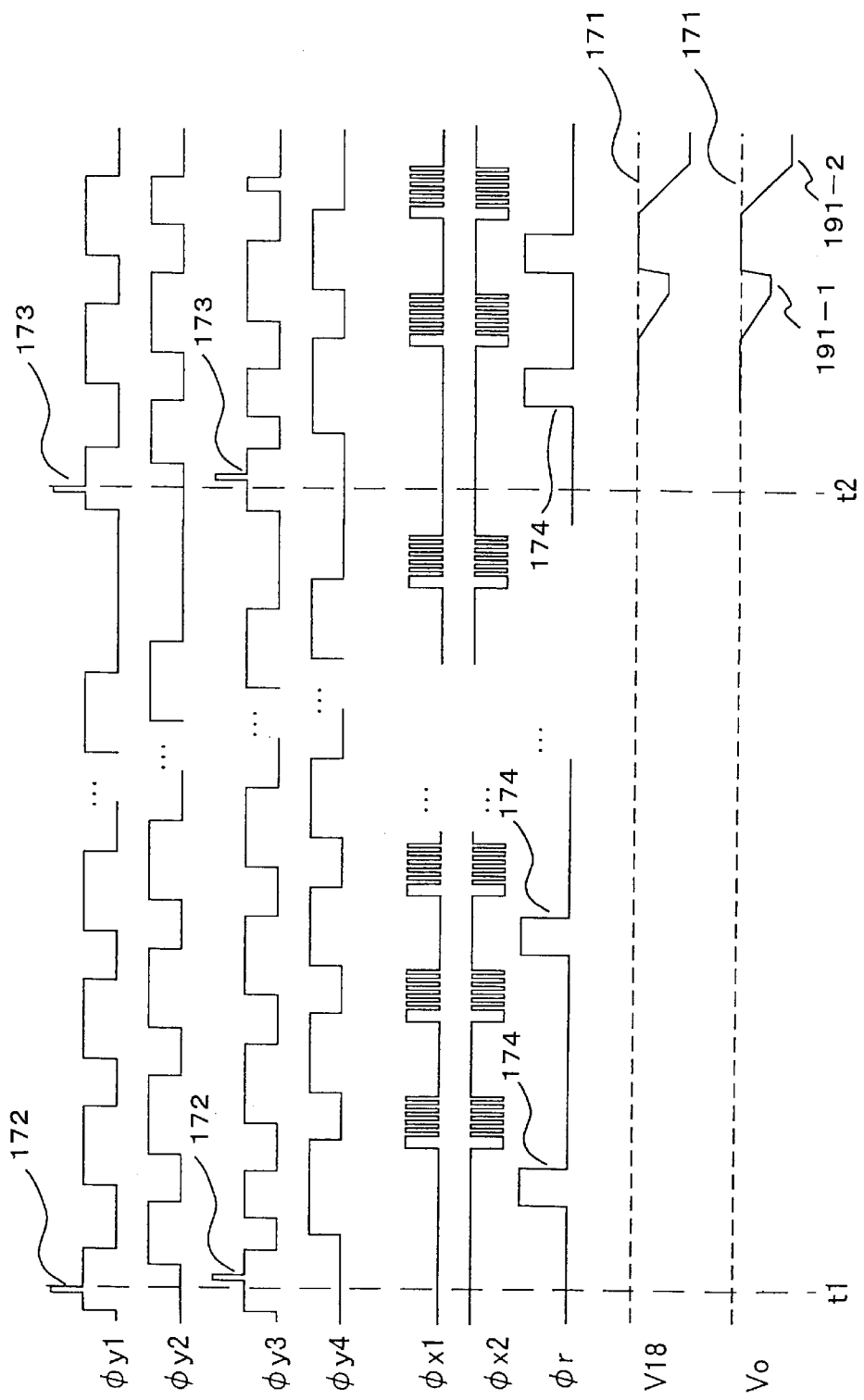
FIG. 19 is a circuit driving timing chart of the device shown in FIG. 18.

FIG. 18 is a plan view illustrating still another example of the fluorescence detecting device of the present invention. FIG. 19 is a driving timing chart of the foregoing device. In these drawings, the same members as those in FIGS. 10 to 15 are designated by the same reference numerals.

As shown in FIG. 18, this device includes a plurality of fluorescence reaction vessels 190-1 and 190-2, and a plurality of photodiodes are provided so that a plurality of the same correspond to each fluorescence reaction vessel. Furthermore, the device is configured so that charges obtained as a result of the photoelectric conversion at the plurality of photodiodes are summed by at least one of the transfer sections and the charge accumulating section.

In this device, charges generated by the photoelectric conversion by the plurality of photodiodes 102 under each fluorescence reaction vessel are summed by applying timing pulses as shown in FIG. 19. First of all, by applying a high-level voltage 172 at a time t1, charges that have been accumulated in the photodiodes are transferred to the Y transfer section 101. Subsequently, in response to pulses φy1 to φy4, φx1, φx2, and φr, the charges are discharged through the reset transistor 107. Thereafter, the accumulation of charges obtained as a result of the photoelectric conversion of a fluorescence starts in the photodiodes. In response to the application of a high-level voltage 173 at a time t2, charges accumulated in the photodiodes 102 are read out to the Y transfer section 101. Then, the pulses φy1 to φy4 are supplied to transfer electrodes of the Y transfer section 101, whereby charges of photodiodes juxtaposed in a Y direction are summed. Subsequently, charges are transferred from the Y transfer section 101 to the X transfer section 103. Next, in response to pulses φx1 and φx2 supplied to transfer electrodes of the X transfer section 103, charges are transferred to the charge accumulating section 104. Here, by supplying the high-level voltage 174 of the reset pulse φr every time a serial transfer operation to the X transfer section 103 is completed, as shown in the drawing, charges of the photodiodes juxtaposed in an X direction are summed in the charge accumulating section 104. The signal voltages 1911 and 191-2 thus obtained at the signal output terminal Vo correspond to respective fluorescences detected at the fluorescence reaction vessels 190-1 and 190-2. Here, a period from a time t1 until a time t2 constitutes a period during which charges obtained as a result of the photoelectric conversion of a fluorescence are accumulated in the photodiodes.

The other configurations, operations, conditions, driving operations, and the like of the foregoing device are identical to those of the device according to the aforementioned fifth or sixth embodiment.

Eighth Embodiment

Figure 20:
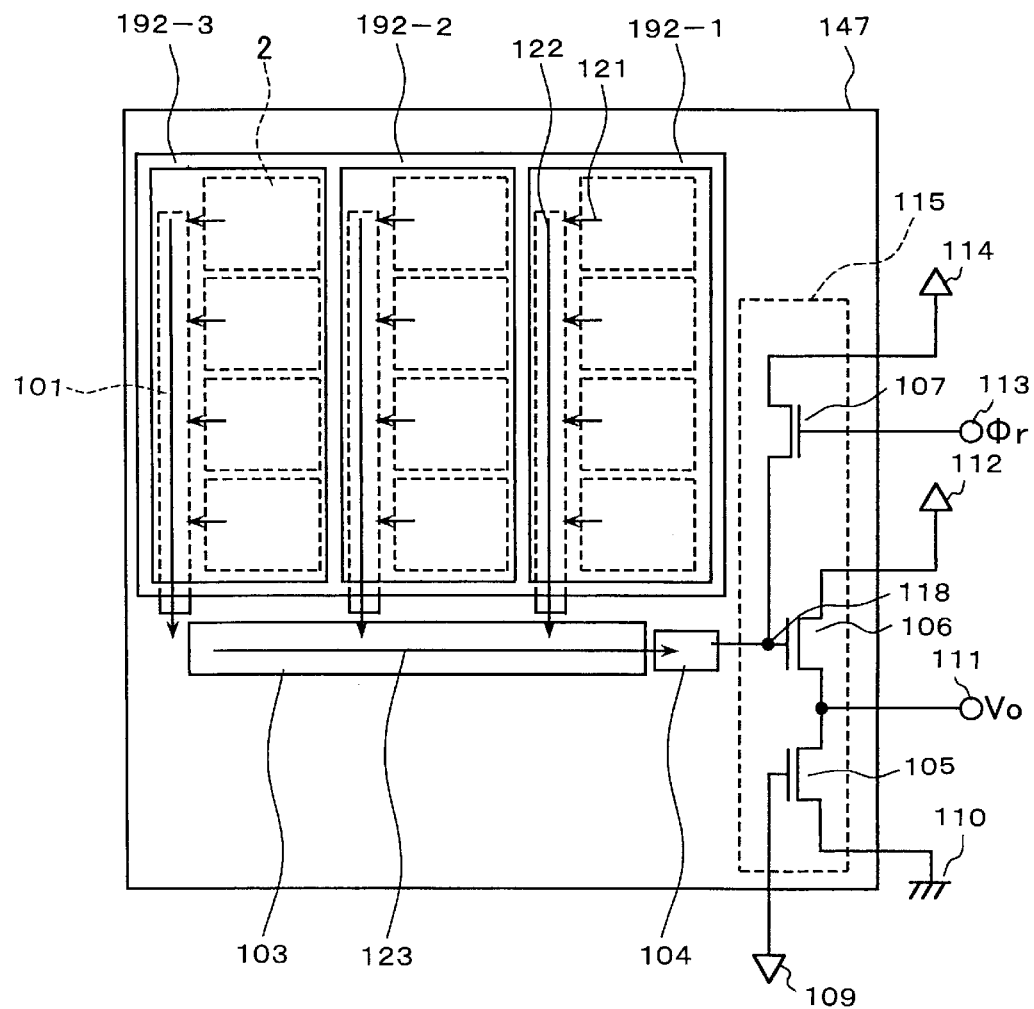
FIG. 20 is a plan view illustrating still another example of a second fluorescence detecting device of the present invention.
Figure 21:
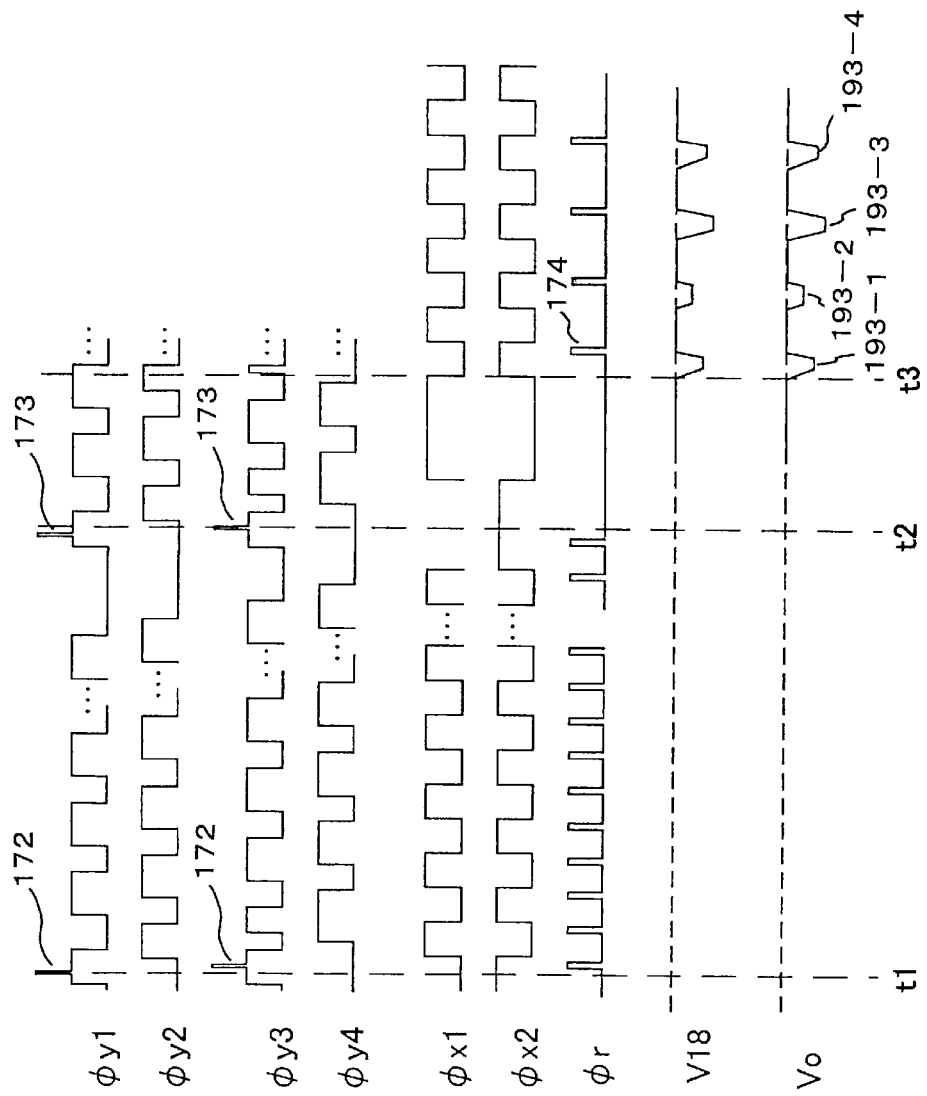
FIG. 21 is a circuit driving timing chart of the device shown in FIG. 20.
Figure 22:
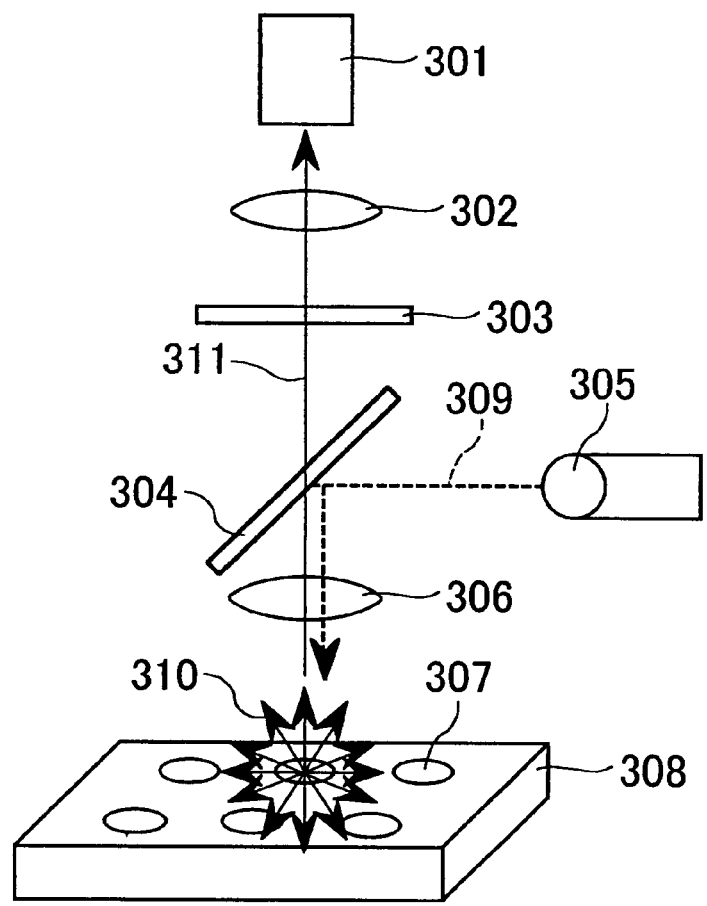
FIG. 22 is a view illustrating a configuration of a conventional fluorescence detecting device.

FIG. 20 is a plan view illustrating still another example of the fluorescence detecting device of the present invention. FIG. 21 is a driving timing chart of this device. In the drawings, the same members as those shown in FIGS. 10 to 15 are designated by the same reference numerals.

As shown in FIG. 20, the foregoing device includes a plurality of fluorescence reaction vessels 192-1, 192-2, and 192-3, and a plurality of photodiodes are provided so that a plurality of the same correspond to each fluorescence reaction vessel. Furthermore, the device is configured so that charges obtained as a result of the photoelectric conversion at the plurality of photodiodes are summed by at least one of the transfer sections and the charge accumulating section. As shown in the drawing, in this device, one fluorescence reaction vessel is provided with respect to each column of the photodiodes arranged in a two-dimensional matrix.

In this device, charges generated by the photoelectric conversion by the plurality of photodiodes 102 under each fluorescence reaction vessel are summed by applying timing pulses as shown in FIG. 21. First of all, by applying a high-level voltage 172 at a time t1, charges that have been accumulated in the photodiodes 102 are transferred to the Y transfer section 101. Subsequently, in response to pulses φy1 to φy4, φx1, φx2, and φr, the foregoing charges are discharged through the reset transistor 107. Thereafter, with the photoelectric conversion of a fluorescence in the photodiodes, the accumulation of charges in the photodiodes starts. In response to the application of a high-level voltage 173 at a time t2, charges accumulated in the photodiodes 102 are read out to the Y transfer section 101. Then, the pulses φy1 to φy4 as shown in the drawing are supplied to transfer electrodes of the Y transfer section 101, whereby charges of photodiodes juxtaposed in a Y direction are summed. Subsequently, charges in the Y transfer section 101 are transferred to the X transfer section 103 column by column. Next, in response to the pulses φx1 and φx2 supplied to transfer electrodes of the X transfer section 103, charges are transferred to the charge accumulating section 104. Here, by supplying the high-level voltage 174 of the reset pulse φr at every clock period of the X transfer section 103, as shown in the drawing, charges of the photodiodes in each column are outputted as signal voltages 193-1, 193-2, and 193-3, respectively. The signal voltages 193-1, 193-2, and 193-3 thus obtained at the signal output terminal Vo correspond to fluorescences detected at the fluorescence reaction vessels 192-1, 192-2, and 192-3, respectively. Here, a period from a time t1 until a time t2 constitutes a period during which charges obtained as a result of the photoelectric conversion of a fluorescence are accumulated in the photodiodes.

The other configurations, operations, conditions, driving operations, and the like of the foregoing device are identical to those of the device according to the aforementioned fifth, sixth, or seventh embodiment.

The foregoing examples may be applied in combination. For instance, by combining the seventh and eighth embodiments, the fluorescence reaction vessels may be arranged two-dimensionally.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A fluorescence detecting device comprising:
   a semiconductor integrated circuit substrate including a photodiode and a signal detecting circuit for detecting charges obtained as a result of photoelectric conversion by the photodiode; and
   a fluorescence reaction vessel where a fluorescence reaction occurs, the fluorescence reaction vessel being arranged above the photodiode.

2. The device according to claim 1, wherein
   the semiconductor integrated circuit substrate includes a plurality of unit cells, each of which is composed of the photodiode and the signal detecting circuit, and a circuit for selecting and driving each of the unit cells, and
   a plurality of the fluorescence reaction vessels are provided so as to correspond to the unit cells, respectively.

3. The device according to claim 1, wherein
   the semiconductor integrated circuit substrate includes a plurality of unit cells, each of which is composed of the photodiode and the signal detecting circuit, and a circuit for selecting and driving each of the unit cells, and
   at least one of the fluorescence reaction vessels is provided so as to be shared by a plurality of the unit cells.

4. The device according to claim 3, wherein a plurality of the fluorescence reaction vessels are provided so that each of the fluorescence reaction vessel is shared by a plurality of the unit cells.

5. The device according to claim 1, wherein a single-strand DNA is fixed on a bottom of the fluorescence reaction vessel.

6. The device according to claim 1, wherein at least one selected from an antibody and an antigen is fixed on a bottom of the fluorescence reaction vessel.

7. A method for producing the fluorescence detecting device according to claim 1, the method comprising:
   preparing a transparent substrate in which a cavity or a hole that serves as the fluorescence reaction vessel is formed, and a semiconductor integrated circuit substrate in which the photodiode and the signal detecting circuit are formed, and
   adhering the transparent substrate and the semiconductor integrated circuit substrate to each other so that the cavity or the hole is positioned above the photodiode.

8. A fluorescence detecting method employing the fluorescence detecting device according to claim 1, the method comprising:
   causing excitation light to enter the fluorescence reaction vessel; and
   detecting a fluorescence generated as a result of the entry of the excitation light by means of the photodiode.

9. The method according to claim 8, wherein the excitation light enters the fluorescence reaction vessel from a side thereof.

10. A fluorescence detecting device comprising:
    a semiconductor integrated circuit substrate including
    a photodiode,
    a charge transfer section for reading out and transferring charges obtained as a result of photoelectric conversion by the photodiode,
    a charge accumulating section for accumulating the charges transferred thereto by the charge transfer section, and
    a signal detecting circuit for detecting charges accumulated in the charge accumulating section; and
    a fluorescence reaction vessel where a fluorescence reaction occurs, the fluorescence reaction vessel being arranged above the photodiode.

11. The device according to claim 10, wherein
    the semiconductor integrated circuit substrate includes
    a plurality of unit cells each of which is composed of the photodiode, the charge transfer section, the charge accumulating section, and the signal detecting circuit, and
    a circuit for selecting and driving each of the plurality of the unit cells, and
    a plurality of the fluorescence reaction vessels are provided so as to correspond to the unit cells, respectively.

12. The device according to claim 10, wherein
    the semiconductor integrated circuit substrate includes a plurality of the photodiodes,
    the fluorescence reaction vessel is arranged so that a plurality of the photodiodes treats a fluorescence from the fluorescence reaction vessel, and
    charges obtained as a result of photoelectric conversion by the plurality of the photodiodes are summed by at least one of the charge transfer section and the charge accumulating section.

13. The device according to claim 12, wherein a plurality of the fluorescence reaction vessels are provided.

14. The device according to claim 10, wherein a single-strand DNA is fixed on a bottom of the fluorescence reaction vessel.

15. The device according to claim 10, wherein at least one selected from an antibody and an antigen is fixed on a bottom of the fluorescence reaction vessel.

16. A method for producing the fluorescence detecting device according to claim 10, the method comprising:
    preparing a transparent substrate in which a cavity or a hole that serves as the fluorescence reaction vessel is formed, and a semiconductor integrated circuit substrate in which the photodiode, the charge transfer section, the charge accumulating section, and the signal detecting circuit are formed, and
    adhering the transparent substrate and the semiconductor integrated circuit substrate to each other so that the cavity or the hole is positioned above the photodiode.

17. A fluorescence detecting method employing the fluorescence detecting device according to claim 10, the method comprising:
    causing excitation light to enter the fluorescence reaction vessel; and
    detecting a fluorescence generated as a result of the entry of the excitation light by means of the photodiode.

18. The method according to claim 17, wherein the excitation light enters the fluorescence reaction vessel from a side thereof.

* * * * *